United States Patent
Peoples et al.

(10) Patent No.: US 11,564,987 B2
(45) Date of Patent: Jan. 31, 2023

(54) COMBINATION IMMUNOTHERAPY FOR TREATMENT OF TRIPLE-NEGATIVE BREAST CANCER

(71) Applicant: SLSG LIMITED LLC, Dover, DE (US)

(72) Inventors: George E. Peoples, San Antonio, TX (US); Angelos M. Stergiou, New York, NY (US); Nicholas J. Sarlis, New York, NY (US)

(73) Assignee: SLSG LIMITED LLC, Dover, DE (US)

( * ) Notice: Subject to any disclaimer, the term of this patent is extended or adjusted under 35 U.S.C. 154(b) by 0 days.

(21) Appl. No.: 16/658,047

(22) Filed: Oct. 19, 2019

(65) Prior Publication Data

US 2020/0121789 A1  Apr. 23, 2020

Related U.S. Application Data

(60) Provisional application No. 62/855,650, filed on May 31, 2019, provisional application No. 62/748,511, filed on Oct. 21, 2018.

(51) Int. Cl.
| | |
|---|---|
| *A61K 39/395* | (2006.01) |
| *A61K 39/00* | (2006.01) |
| *A61P 35/00* | (2006.01) |
| *A61K 9/00* | (2006.01) |
| *A61K 39/39* | (2006.01) |

(52) U.S. Cl.
CPC ...... *A61K 39/39558* (2013.01); *A61K 9/0019* (2013.01); *A61K 39/001106* (2018.08); *A61K 39/39* (2013.01); *A61P 35/00* (2018.01); *A61K 2039/54* (2013.01); *A61K 2039/545* (2013.01); *A61K 2039/55522* (2013.01); *A61K 2039/812* (2018.08)

(58) Field of Classification Search
CPC ...... A61K 39/39558; A61K 39/001106; A61K 2039/812; A61K 2039/55522
See application file for complete search history.

(56) References Cited

U.S. PATENT DOCUMENTS

| | | | |
|---|---|---|---|
| 5,821,337 A | 10/1998 | Carter et al. | |
| 8,222,214 B2 | 7/2012 | Peoples et al. | |
| 8,796,220 B2 | 8/2014 | Peoples et al. | |
| 8,802,618 B2 | 8/2014 | Ioannides et al. | |
| 8,883,164 B2 | 11/2014 | Ponniah et al. | |
| 9,370,560 B2 | 6/2016 | Peoples et al. | |
| 10,239,916 B2 | 3/2019 | Ioannides et al. | |
| 10,842,856 B2 | 11/2020 | Peoples et al. | |
| 2008/0260745 A1* | 10/2008 | Ponniah | G01N 33/577 424/139.1 |
| 2010/0316640 A1 | 12/2010 | Sundaram et al. | |
| 2015/0182609 A1* | 7/2015 | Peoples | A61K 9/0019 424/185.1 |

FOREIGN PATENT DOCUMENTS

| | | | |
|---|---|---|---|
| WO | WO 2001/000024 | 1/2001 | |
| WO | WO 2016/164833 | 10/2016 | |
| WO | WO 2016/196373 | 12/2016 | |
| WO | WO-2017184597 A1 * | 10/2017 | ............... A61P 35/00 |

OTHER PUBLICATIONS

NCT01570036, https://clinicaltrials.gov/ct2/history/NCT01570036, Publication Date: Aug. 14, 2017 (Year: 2017).*
Triple Negative Breast Cancer, https://www.cdc.gov/cancer/breast/triple-negative.htm (Year: 2020).*
Kono et al., Trastuzumab (Herceptin) Enhances Class I-Restricted Antigen Presentation Recognized by HER-2/neu-Specific T Cytotoxic Lymphocytes, Clinical Cancer Research, 10, 2538-2544, Publication Date: Apr. 1, 2004 (Year: 2004).*
Tannock, 19 Experimental Chemotherapy, The Basic Science of Oncology, 2nd Edition, Publish Year:1992 (Year: 1992).*
Kwa et al., Checkpoint Inhibitors in Triple-Negative Breast Cancer (TNBC): Where to Go From Here, Cancer 124:2086-2103, Publication Date:Feb. 9, 2018 (Year: 2018).*
Soliman et al., Immunotherapy Strategies in the Treatment of Breast Cancer, Cancer Control, 20:17-21, Publication Date: Jan. 2013 (Year: 2013).*
Brossart, P. et al. "Induction of cytotoxic T-lymphocyte responses in vivo after vaccinations with peptide-pulsed dendritic cells" *Blood*, 2000, 96(1):3102-3108.
Chick, R. et al. "Subgroup analysis of nelipepimut-S plus GM-CSF combined with trastuzumab versus trastuzumab alone to prevent recurrences in patients with high-risk, HER2 low-expressing breast cancer" *Clinical Immunology*, Apr. 2021 (Epub Jan. 2021), 225:108679 (8 pages).

(Continued)

*Primary Examiner* — Peter J Reddig
*Assistant Examiner* — Cheng Lu
(74) *Attorney, Agent, or Firm* — Saliwanchik, Lloyd & Eisenschenk

(57) ABSTRACT

The present invention concerns a method for treating triple-negative breast cancer (TNBC) in an individual, and/or for inducing an immune response to HER2/neu in an individual with a triple-negative breast cancer expressing low levels of HER2/neu, the method comprising administering to the individual: (a) an effective amount of trastuzumab, or derivative thereof; and (b) an effective amount of nelipepimut-S, or variant thereof, optionally with an immunological adjuvant. Preferably, the method includes a preparatory or priming phase comprising a frequency and duration of trastuzumab or trastuzumab derivative administration sufficient to substantially increase the major histocompatibility complex (MHC)-mediated presentation of HER2 peptide fragments to the patient immune system. The invention also includes medicaments and kits for treating TNBC in an individual, and/or for inducing an immune response to HER2/neu in an individual with a TNBC expressing HER2/neu.

22 Claims, 9 Drawing Sheets

Specification includes a Sequence Listing.

(56) References Cited

OTHER PUBLICATIONS

Clifton, G. et al. "Results of a Randomized Phase IIb Trial of Nelipepimut-S + Trastuzumab versus Trastuzumab to Prevent Recurrences in Patients with High-Risk HER2 Low-Expressing Breast Cancer" *Clin Cancer Res.*, 2020, 26:2515-2523.
Conrad, H. et al. "CTLs Directed against HER2 Specifically Cross-React with HER3 and HER4" *J Immunol.*, 2008, 180(12):8135-8145.
Disis, M.L. et al. "Generation of T-cell immunity to the HER-2/neu protein after active immunization with HER-2/neu peptide-based vaccines" *J Clin Oncol.*, 2002, 20(11):2624-2632.
Disis, M.L et al. "Generation of Immunity to the HER-2/neu Oncogenic Protein in Patients with Breast and Ovarian Cancer Using a Peptide-based Vaccine" *Clin Cancer Res.*, 1999, 5(6):1289-1297.
Emens, L.A. et al. "Breast cancer vaccines: maximizing cancer treatment by tapping into host immunity" *Endocr Relat Cancer.*, 2005, 12(1):1-17.
Fehrenbacher, L. et al. "NSABP B-47 (NRG oncology): Phase III randomized trial comparing adjuvant chemotherapy with adriamycin (A) and cyclophosphamide (C) → weekly paclitaxel (WP), or docetaxel (T) and C with or without a year of trastuzumab (H) in women with node-positive or high-risk node-negative invasive breast cancer (IBC) expressing HER2 staining intensity of IHC 1 + or 2+ with negative FISH (HER2-Low IBC)" Abstract GS1-02 presented at the 2017 San Antonio Breast Cancer Symposium, Dec. 5-9, 2017.
Gall, V. et al. "Trastuzumab Increases HER2 Uptake and Cross-Presentation by Dendritic Cells" *Cancer Res.*, 2017, 77(19):5374-5383.
Gutierrez, C et al. "HER2: Biology, Detection, and Clinical Implications" *Arch Pathol Lab Med.*, 2011, 135:55-62.
Hale, D.F. et al. "Pre-specified interim analysis of a randomized phase 2b trial of trastuzumab + nelipepimut-S (NeuVax) vs trastuzumab for the prevention of recurrence demonstrates benefit in triple negative (HER2 low-expressing) breast cancer patients" *Annals of Oncology*, 2018, 29(suppl_8):viii400-viii441, Abstract 2132.
Hale, D.F. et al. "Pre-specified interim analysis of a randomized phase 2b trial of trastuzumab + nelipepimut-S (NeuVax) vs trastuzumab for the prevention of recurrence demonstrates benefit in triple negative (HER2 low-expressing) breast cancer patients" poster presented at the 2018 Annual Meeting of the European Society for Medical Oncology, Oct. 19-23 in Munich, Germany.
Hickerson, A. et al. "Correlation between response and HLA type in a randomized phase IIb trial of NeuVax + trastuzumab in HER2 low-expressing breast cancer patients to prevent recurrence" poster presented at the 2018 Society for Immunotherapy of Cancer (SITC) Annual Meeting, Nov. 9-11, 2018 in Washington, D.C.
Mittendorf, E. et al. "Final report of the phase I/II clinical trial of the E75 (nelipepimut-S) vaccine with booster inoculations to prevent disease recurrence in high-risk breast cancer patients" *Ann Oncol.*, 2014, 25(9):1735-1742.
Mittendorf, E. et al. "Investigating the Combination of Trastuzumab and HER2/neu Peptide Vaccines for the Treatment of Breast Cancer" *Annals of Surgical Oncology*, 2006, 13(8):1085-1098.
Mittendorf, E. et al. "Vaccination with a HER2/neu peptide induces intra- and inter-antigenic epitope spreading in patients with early stage breast cancer" *Surgery*, 2006, 139(3):407-418.
Peoples, G.E. et al. "Combined clinical trial results of a HER2/neu (E75) vaccine for the prevention of recurrence in high-risk breast cancer patients: U.S. Military Cancer Institute Clinical Trials Group Study I-01 and I-02" *Clin Cancer Res.* 2008, 14(3):797-803.
Selis, F. et al. "Pegylated Trastuzumab Fragments Acquire an Increased in Vivo Stability but Show a Largely Reduced Affinity for the Target Antigen" *Int J Mol Sci.*, 2016, 17(4):491 (15 pages).
SELLAS press release dated Oct. 2, 2018, "SELLAS to Present Data from Phase 2b Trial of NeuVax + Herceptin® at the 2018 Society for Immunotherapy of Cancer (SITC) Annual Meeting".
Wolff, A. et al. "Human Epidermal Growth Factor Receptor2 Testing in Breast Cancer: American Society of Clinical Oncology/College of American Pathologists Clinical Practice Guideline Focused Update" *J Clin Oncol.*, 2018, 36(20):2105-2122.
Extended European Search Report, dated Jun. 30, 2022, issued in European Patent Application No. 19876203.1.
Costa, R. et al. "Targeting epidermal growth factor receptor in triple negative breast cancer: New discoveries and practical insights fordrug development" *Cancer Treatment Reviews*, 2017, 53:111-119.
De La Cruz, L.M. and Czerniecki, B.J. "Immunotherapy for breast cancer is finally at the doorstep: Immunotherapy in breast cancer" *Ann. Surg. Oncol.*, 2018, 25:2852-2857.
Jackson, D.O. et al. "Interim safety analysis of a phase II trial combining trastuzumab and NeuVax, a HER2-targeted peptide vaccine, to prevent breast cancer recurrence in HER2 low expression" *Annals of Oncology*, 2016, 27(Supplement 6):vi359-vi378, abstract 1069P (1 page).
Schneble, E.J. et al. "Abstract 2558: HLA-A2 and HER2 expression levels as clinical prognostic factors in breast cancer patients: implications for peptide cancer vaccine trials" *Cancer Res.*, 2014, 74(19_Supplement):2558.
Clifton, G.T. et al. "Initial safety analysis of a randomized phase II trial of nelipepimut-S + GM-CSF and trastuzumab compared to trastuzumab alone to prevent recurrence in breast cancer patients with HER2 low-expressing tumors" *Clinical Immunology*, 2019, 201:48-54.

\* cited by examiner

COMBINATION IMMUNOTHERAPY FOR TREATMENT OF TRIPLE-NEGATIVE BREAST CANCER

CROSS-REFERENCE TO RELATED APPLICATIONS

The present application claims the benefit of U.S. Provisional Application Ser. No. 62/855,650, filed May 31, 2019, and 62/748,511, filed Oct. 21, 2018, each of which is hereby incorporated by reference herein in its entirety, including any figures, tables, nucleic acid sequences, amino acid sequences, or drawings.

BACKGROUND OF THE INVENTION

The current standard of care for breast cancer includes screening the tumor for the expression levels of the hormone receptors, estrogen receptor (ER), and progesterone receptor (PR), and the human epidermal growth factor receptor 2 (HER2) kinase. A woman diagnosed with breast cancer may be treated preliminarily with surgery, chemotherapy (optional in some cases), and radiation therapy before targeted therapy is initiated.

Hormone receptor-positive breast cancers are susceptible to hormone therapies with selective estrogen receptor modulators or SERMs (e.g., tamoxifen, toremifene), aromatase inhibitors (e.g., anastrozole), or selective estrogen receptor degraders or SERDs (e.g., fulvestrant). Hormone therapies such as aromatase inhibitors (AI) block production of estrogens in the body (typically used in post-menopausal women), whereas SERMs and SERDs block the proliferative action of estrogens on the breast cancer cells. Hormone receptor-positive and HER2-negative patients that have failed initial hormone therapy are often treated with an inhibitor of cyclin-dependent kinase (CDK) types 4 and 6 (CDK4/6 inhibitor) palbociclib (Ibrance) in combination with either letrozole or fulvestrant. HER2-positive breast cancers are susceptible to HER2 kinase inhibitors (e.g., trastuzumab and lapatinib) and are generally used in metastatic disease. Despite these multiple tiers of targeted treatments, patients often have or develop refractory forms of breast cancer.

Examples of refractory breast cancer include primary tumors which are triple-negative (lacking ER, PR, and HER2), hormone resistant (SERM-, SERD-, or AI-resistant), or kinase inhibitor resistant, or metastatic breast cancer tumors. Once the targeted therapies fail or tumors metastasize, radiation and high dose chemotherapy are required to ablate the refractory breast cancer tumors. Chemotherapies available for the treatment of refractory breast cancer include anthracyclines, taxanes, and epothilones, which are toxic, involve risk, are costly, and often are ineffective, especially in the treatment of metastatic disease.

Patients having HER2 low-expressing breast cancer, as defined as HER2 immunohistochemistry (IHC) 1+ or 2+, are not currently eligible for adjuvant therapy with trastuzumab. Adding trastuzumab (currently marketed in the United States as Herceptin®) to standard adjuvant chemotherapy did not improve invasive disease-free survival for patients with early-stage breast cancer found to have low levels of HER2, according to data from the randomized, phase III National Surgical Adjuvant Breast and Bowel Project (NSABP) B-47. Therefore, HER2 low-expressing breast cancer patients are currently ineligible for HER2-directed therapy with trastuzumab monotherapy. Current guidelines classify a breast cancer as "HER2 positive" if immunohistochemistry (IHC) testing shows it has high levels of HER2 protein, defined as IHC 3+, or fluorescence-based in situ hybridization (FISH) shows it has increased numbers of copies of the HER2 gene, defined as FISH-positive.

Although the majority of breast cancers are considered hormone receptor-positive (ER, PR), or are HER2-positive, 15-20% of women diagnosed with breast cancer will have triple negative breast cancer (TNBC) which is characterized by a lack of expression of ER, PR, or high levels of expression of HER2. TNBC occurs more frequently in younger patients (<50 years of age) and generally shows a more aggressive behavior. For those patients with advanced TNBC, standard palliative treatment options are limited to cytotoxic chemotherapy. However, even after initial response to chemotherapy, the duration of the response may be short and there is a higher likelihood of visceral metastases, rapidly progressive disease, and inferior survival compared to hormone positive breast cancer. Of note, there is a high rate of relapse in patients with early-stage TNBC after standard front-line therapy—currently, typically including neoadjuvant or adjuvant chemotherapy, surgical tumor extirpation and, in select cases, radiotherapy. Despite that, no targeted therapy, chemotherapy or immunotherapy has been proven to be active in the adjuvant/maintenance setting (i.e., after completion of the front-line therapy) in delaying or preventing such relapses. Therefore, new treatment approaches are needed to benefit patients suffering from difficult-to-treat cancers such as TNBC, both in the metastatic, but also importantly the adjuvant setting in early-stage disease.

BRIEF SUMMARY OF THE INVENTION

The present invention concerns a method for treating triple-negative breast cancer (TNBC) in an individual, and/or for inducing an immune response to HER2/neu in an individual with a triple-negative breast cancer, i.e., cancer which is hormone receptor-negative but is also expressing low levels of HER2/neu (e.g., 1+ or 2+ by IHC), the method comprising administering to the individual: (a) an effective amount of trastuzumab (TZ), or derivative thereof; and (b) an effective amount of nelipepimut-S (NPS), or variant thereof. In some embodiments, the method further includes administering an immunologic adjuvant to the individual, such as granulocyte-macrophage colony stimulating factor (GM-CSF). The invention also includes medicaments and kits for treating TNBC in an individual, and/or for inducing an immune response to HER2/neu in an individual with a TNBC expressing low levels of HER2/neu (e.g., 1+ or 2+ by IHC).

One aspect of the invention concerns a method for treating triple-negative breast cancer (TNBC) in an individual, comprising administering to the individual: (a) an effective amount of trastuzumab, or derivative thereof, and (b) an effective amount of nelipepimut-S, or variant thereof. In some embodiments, the trastuzumab, or derivative thereof, and the nelipepimut-S, or variant thereof, are administered at intervals, and administration of the nelipepimut-S, or variant thereof, is initiated after initiation of administration of the trastuzumab or derivative thereof. In some embodiments, the method comprises initiation of a preparatory phase comprising periodic administration of doses of trastuzumab, or derivative thereof, without nelipepimut-S or variant, followed by a combination phase comprising periodic administration of doses of both the trastuzumab, or derivative thereof, and nelipepimut-S or variant. In some embodiments, the individual is node-negative, and/or the TNBC has a HER2 expression of 1-2+ by IHC. In some embodiments, the method further comprises administering an immunologic adjuvant, such as granulocyte-macrophage colony stimulating factor (GM-CSF), which may be administered in the same formulation as the nelipepimut-S, or variant thereof, or within a separate formulation. Optionally, booster inoculations with nelipepimut-S for a period of up to 30 months or longer may be employed, in which the administration of the nelipepimut-S or variant thereof represents a primary vaccination phase, and wherein the method further comprises, after completion of the primary vaccination, administering 1, 2, 3, 4, or more doses of nelipepimut-S or variant thereof (booster administration phase), optionally with an immunologic adjuvant (e.g., GM-CSF), at a lesser frequency than the primary vaccination. For example, two or more booster doses of nelipepimut-S or variant thereof may be administered, in which one booster dose is administered every 6 months. FIG. 2 shows a schematic of a treatment regimen with an embodiment in which an immunologic adjuvant (GM-CSF) and booster doses are employed (see the treatment arm of NeuVax (NPS+GM-CSF)+TZ).

Another aspect of the invention concerns a method of inducing an immune response to HER2/neu in an individual with a triple-negative breast cancer expressing low levels of HER2/neu, the method comprising administering to the individual: (a) an effective amount of trastuzumab, or derivative thereof, and (b) an effective amount of nelipepimut-S, or variant thereof. In some embodiments, the trastuzumab, or derivative thereof, and the nelipepimut-S, or variant thereof, are administered at intervals, and administration of the nelipepimut-S, or variant thereof, is initiated after initiation of administration of the trastuzumab, or derivative thereof. In some embodiments, the method comprises initiation of a preparatory phase comprising periodic administration of doses of trastuzumab, or derivative thereof, without nelipepimut-S or variant, followed by a combination phase comprising periodic administration of doses of both the trastuzumab or derivative and nelipepimut-S or variant. In some embodiments, the individual is node-negative, and/or the TNBC has a HER2 expression of 1+ or 2+ by IHC. In some embodiments, the method further comprises administering an immunologic adjuvant, such as granulocyte-macrophage colony stimulating factor (GM-CSF), which may be administered in the same formulation as the nelipepimut-S, or variant thereof, or within a separate formulation. Optionally, booster inoculations with NPS or a variant thereof for a period of up to 30 months or longer may be employed, in which the administration of the NPS or variant thereof represents a primary vaccination phase, and wherein the method further comprises, after completion of the primary vaccination, administering 1, 2, 3, 4, or more doses of nelipepimut-S or variant thereof (booster administration phase), optionally with an immunologic adjuvant (e.g., GM-CSF), at a lesser frequency than the primary vaccination. For example, two or more booster doses of nelipepimut-S or variant thereof may be administered, in which one booster dose is administered every 6 months. FIG. 2 shows a schematic of a treatment regimen with an embodiment in which an immunologic adjuvant (GM-CSF) and booster doses are employed (see the treatment arm of NeuVax (NPS+GM-CSF)+TZ).

In some embodiments of the methods of the invention, the individual is HLA-A2 positive, HLA-A3 positive, HLA-A24 positive, or HLA-A26 positive.

Another aspect of the invention concerns a medicament comprising nelipepimut-S, or variant thereof, for use in combination with trastuzumab, or derivative thereof, for treating triple-negative breast cancer in an individual. Optionally, the medicament can further include an immunologic adjuvant, such as GM-CSF.

Another aspect of the invention concerns a medicament comprising trastuzumab, or a derivative thereof, for use in combination with nelipepimut-S, or variant thereof, for treating triple-negative breast cancer in an individual.

Another aspect of the invention concerns a kit having a first container, a second container, and a package insert, wherein the first container comprises at least one dose of a medicament comprising trastuzumab, or a derivative thereof, the second container comprises at least one dose of a medicament comprising nelipepimut-S, or variant thereof, and the package insert comprises instructions for treating an individual for triple-negative breast cancer using the medicaments. Optionally, the kit can further include an immunologic adjuvant, such as GM-CSF, wherein the immunologic adjuvant is in a third container or is in the second container with the nelipepimut-S, or variant thereof.

BRIEF DESCRIPTION OF THE SEQUENCES

Figure 1:
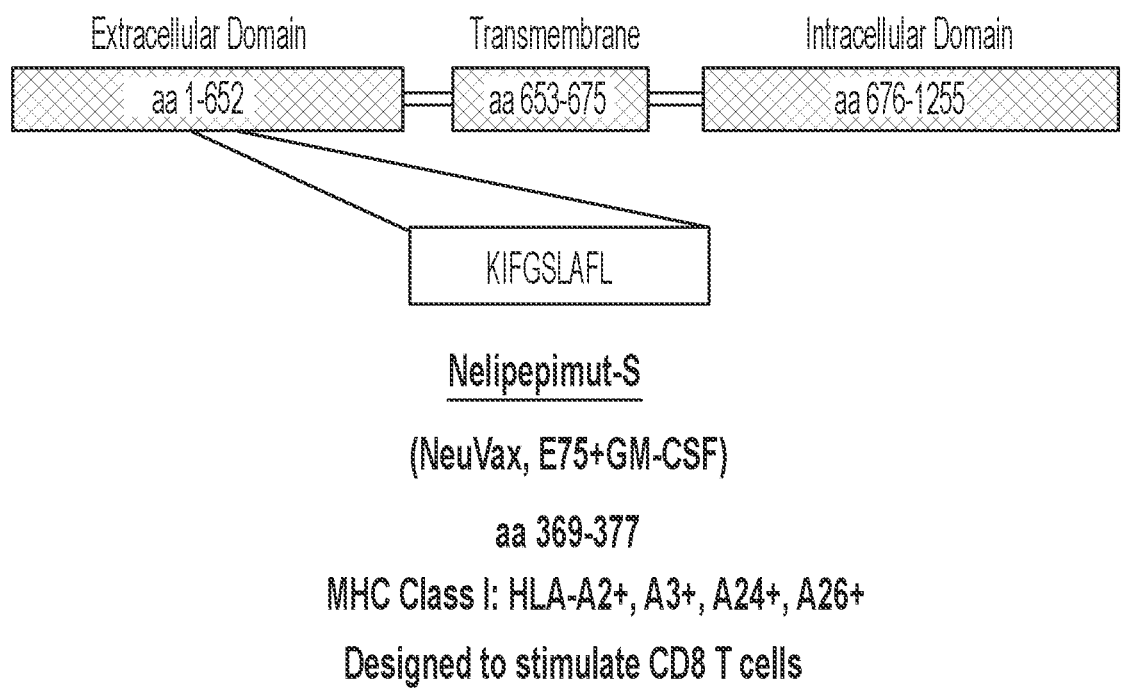
FIG. 1 shows a schematic of the HER2 protein and the region (amino acids 369-377) from which the 9-mer nelipepimut-S peptide (KIFGSLAFL) (SEQ ID NO:1) is derived. The NeuVax™ HER-2/neu peptide vaccine includes the nelipepimut-S peptide and the immunologic adjuvant GM-CSF (Mittendorf E. et al. *Ann Oncol.*, 2014, 25:1735-42). aa—amino acid; GM-CSF—granulocyte macrophage colony-stimulating factor; HER2—human epidermal growth factor receptor 2; HLA—human leukocyte antigen; MHC—major histocompatibility complex; TZ—trastuzumab.

SEQ ID NO:1 is the nelipepimut-S peptide: KIFGSLAFL.
SEQ ID NO:2 is a variant of the nelipepimut-S peptide, having an alpha-aminobutyric acid at position 4: K I F Abu S L A F L.
SEQ ID NO:3 is a variant of the nelipepimut-S peptide, having a norvaline at position 4: K I F Nva S L A F L.
SEQ ID NO:4 is a variant of the nelipepimut-S peptide, having a norleucine at position 4: K I F Nle S L A F L.
SEQ ID NO:5 is a variant of the nelipepimut-S peptide, having an alpha-aminobutyric acid at position 7: K I F G S L Abu F L.
SEQ ID NO:6 is a variant of the nelipepimut-S peptide, having a norvaline at position 7: K I F G S L Nva F L.
SEQ ID NO:7 is a variant of the nelipepimut-S peptide, having a norleucine at position 7: K I F G S L Ne F L.
SEQ ID NO:8 is a variant of the nelipepimut-S peptide, having an isophenylalanine at position 8: K I F G S L A isoF L.
SEQ ID NO:9 is an amino acid sequence of trastuzumab light chain (anti-HER2 Light chain (1 and 2)).
SEQ ID NO:10 is an amino acid sequence transtuzumab heavy chain (anti-HER2 Heavy chain (1 and 2)).

DETAILED DESCRIPTION OF THE INVENTION

The present invention concerns a method for treating triple-negative breast cancer (TNBC) in an individual, and/or for inducing an immune response to HER2/neu in an individual with a TNBC expressing HER2/neu, the method comprising administering to the individual: (a) an effective amount of trastuzumab, or a derivative thereof; and (b) an effective amount of nelipepimut-S, or variant thereof. In some embodiments, the trastuzumab, or a derivative thereof, and the nelipepimut-S, or a variant thereof, are administered at intervals, and administration of the nelipepimut-S, or variant thereof, is initiated after initiation of administration of the trastuzumab, or derivative thereof. For example, the method may include initiation of a preparatory phase comprising periodic administration of doses of trastuzumab, or derivative thereof, without nelipepimut-S or variant, followed by a combination phase comprising periodic administration of doses of both the trastuzumab or derivative, and nelipepimut-S or variant. In some embodiments, the administration of the nelipepimut-S or variant is initiated after completion of the third, fourth, or fifth administration of trastuzumab or derivative. In some embodiments, the trastuzumab or derivative thereof is administered at an initial loading dose of 8 mg/kg and maintenance doses of 6 mg/kg every three weeks (q3wk), and wherein a dose of 1,000 mcg of the nelipepimut-S or variant is administered.

In some embodiments, the preparatory phase comprises a frequency and duration of administration of trastuzumab, or derivative thereof (prior to vaccination with nelipepimut-S) sufficient to increase the presentation, in a major histocompatibility complex (MHC) type I context, of various HER2 protein peptide fragments (including the peptide with an amino acid sequence identical to that of nelipepimut-S or variant thereof, i.e., the vaccine's antigen target) onto the breast cancer cell's membrane (bound to human leukocyte antigen [HLA] molecules) to the host's (patient's) immune system. Once this trastuzumab-induced, or derivative-induced, HER2 antigen presentation has been substantially increased on breast cancer cells in the patient, subsequent administration of the nelipepimut-S or variant thereof (through activation of antigen-presenting cells and engagement of naïve CD8+ T-lymphocytes on the immune synapse in the patient) leads to induction, activation, and proliferation of cytotoxic T-lymphocytes (CTLs) against this antigen on the patient's breast cancer cells. This leads to immunologically mediated killing of HER2-expressing breast cancer cells in the patient. Therefore, by using a preparatory phase with the administration sequence or schedule of these two agents (trastuzumab, or derivative thereof, given first, followed by nelipepimut-S or a variant thereof), one ensures that the two agents are optimally synergistic, i.e., with trastuzumab or derivative pre-treatment promoting antigenicity and immunogenicity, thus acting as a pharmacodynamic enhancer of the immunologically mediated action of the nelipepimut-S or variant thereof in the individual.

Figure 2:
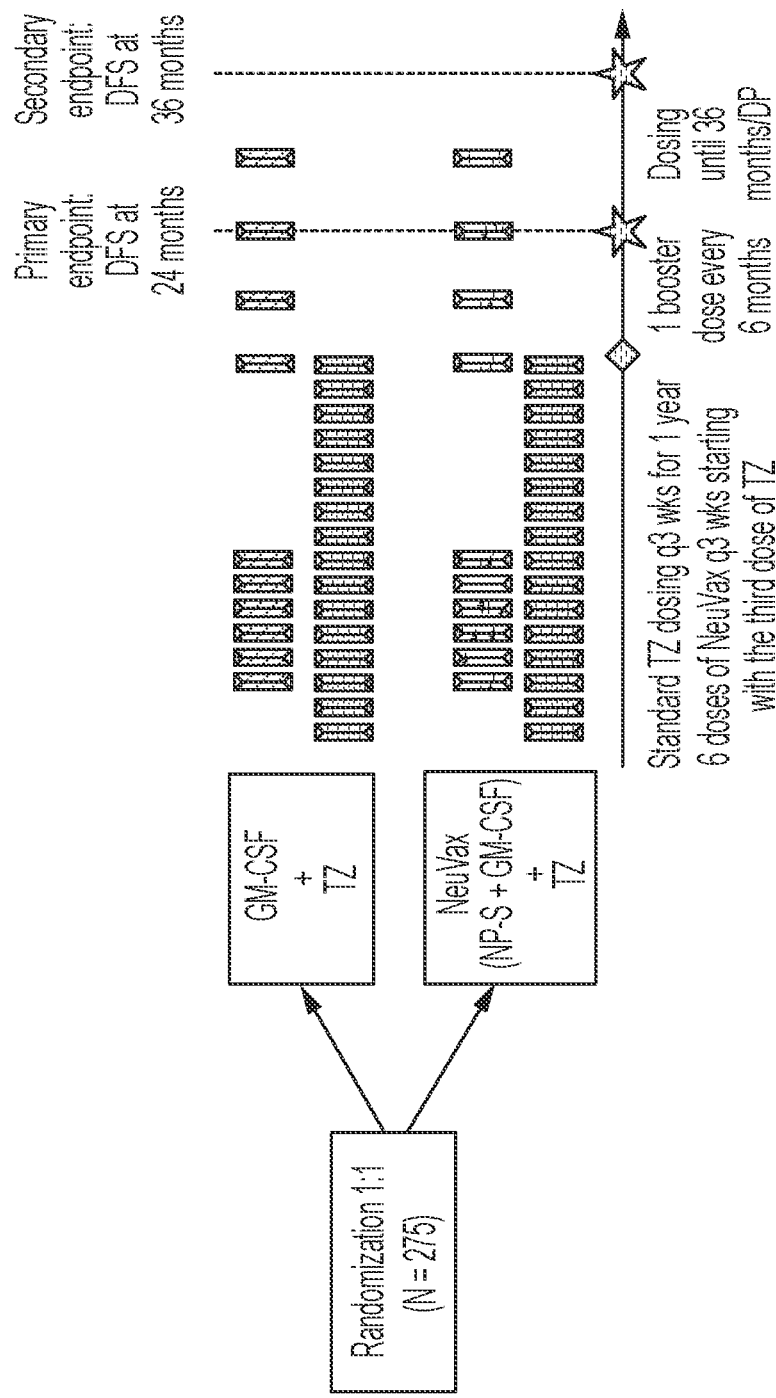
FIG. 2 shows the study design for the human clinical trial investigating whether a combination of trastuzumab and the NeuVax™ vaccine (nelipepimut-S plus GM-CSF) can delay or prevent disease recurrence in patients with HER2 low-expressing tumors, including TNBC tumors. The study design includes the treatment arm using the combination of the NeuVax™ vaccine (NPS+GM-CSF) and trastuzumab (TZ), which represents an embodiment of the methods of the invention for treatment of triple-negative breast cancer and/or for inducing an immune response to HER2/neu in an individual with triple-negative breast cancer. DFS—disease-free survival; DP—disease progression; GM-CSF—granulocyte macrophage colony-stimulating factor; HER2—human epidermal growth factor receptor 2; IHC—immunohistochemistry; NPS—nelipepimut-S; q3 wks—every 3 weeks; TZ—trastuzumab.

The combination treatment arm in the study design depicted in FIG. 2 and described in the Material & Methods and Example herein, which uses the combination of the NeuVax™ vaccine (NPS+GM-CSF) and trastuzumab (TZ), represents an embodiment of the methods of the invention for treatment of triple-negative breast cancer and/or for inducing an immune response to HER2/neu in an individual with triple-negative breast cancer. Other doses, frequencies of doses, and durations of treatment can be determined. For example, ex vivo assays that are essentially variants of a mixed lymphocytic reaction (MLR) can be used to determine other doses, frequencies, and durations of trastuzumab, or derivative thereof, that would be sufficient for the priming phase in a given patient, or group of patients. Peripheral blood mononuclear cells (PBMCs) that include antigen-specific T-lymphocytes can be co-incubated with breast cancer cell lines expressing HER2 in the presence of varying concentrations of trastuzumab in the incubation media. There is a dose-relationship between the in vitro trastuzumab dose used in the experiments and breast cancer cell lysis through activated CTLs. The in vitro methods for these assays are described in the "Methods" section of Gall V A, et al., *Cancer Res.,* 2017 Oct. 1; 77(19):5374-5383, and Mittendorf E A, et al., *Ann Surg Oncol.,* 2006 August; 13(8):1085-98, which are incorporated herein by reference in their entireties. These tests assume that PBMCs are from vaccinated patients, who have received about 3 or 4 initial vaccinations in clinical trials of patients who underwent NeuVax vaccine only therapy (i.e., monotherapy), which is commensurate with the early immunization phase, corresponding to 6 to 8 weeks after initiation of the vaccine.

Elements for the MLR ex vivo are described briefly below:

(1) HER2-low-expressing breast cancer cell lines (including TNBC phenotype breast cancer cell lines);

(2) Solution of trastuzumab or derivative in cell culture media (various concentrations of trastuzumab); and (3) PBMCs (in essence, T-lymphocytes from NPS or variant-vaccinated patients).

(1)+(2), in various in vitro concentrations/doses, are co-incubated. Next, (3) is added in various abundance levels of T-lymphocytes. This would correspond to/simulate a clinical sequence of administration of trastuzumab or a derivative thereof, followed by NPS or a variant thereof.

Another option would be to carry out: (1)+(3), followed by (2). This would correspond to/simulate a clinical sequence of administration of NPS, or a variant thereof, followed by trastuzumab, or derivative thereof.

Another option would be to carry out: (1)+(2)+(3) simultaneously, then (2). This would correspond to/simulate simultaneous co-administration of NPS, or variant thereof, with trastuzumab, or derivative thereof.

In some embodiments of the methods of the invention, the TNBC has a HER2 expression of 1+ or 2+ by IHC.

In some embodiments of the methods of the invention, the individual is HLA-A2 positive, HLA-A3 positive, HLA-A24 positive, or HLA-A26 positive.

In some embodiments of the methods of the invention, the individual is HLA-A24 positive. As described in Example 2, HLA-A24+ TNBC patients had a significant improvement in disease free survival despite the lowest predicted binding potential between E75 and this HLA-type. In fact, the strongest clinical effect ever seen with the NPS plus trastuzumab combination was in HLA-A24+ patients, both for the TNBC cohort and the ITT population (the latter being HER2 IHC 1+/2+ irrespective of hormone receptor status). HLA-A24 is the most heavily expressed HLA type in populations living in the Asian/Pacific basin region.

In some embodiments of the methods of the invention, the individual is clinically disease (cancer)-free at the time of said administering, after receiving therapy for the TNBC, such as standard of care therapy (e.g., surgery, chemotherapy, radiation therapy, or a combination of two or more of the foregoing). In some embodiments, administration of trastuzumab, or derivative thereof, is initiated between three weeks and twelve weeks after completion of the standard of care therapy. The TNBC may be node-positive or node-negative. In some embodiments, the TNBC is node-negative (e.g., AJCC N0 or N0(i+)) at the time of said administering.

In other embodiments, the individual is not cancer-free at the time of said administering.

In some embodiments, trastuzumab is administered. In some embodiments, a derivative of trastuzumab is administered. The trastuzumab, or derivative thereof, may be administered to the individual by any effective method. In some embodiments, the trastuzumab, or derivative thereof, is administered intravenously.

The nelipepimut-S, or variant thereof, may be administered to the individual by any effective method and route. The nelipepimut-S, or variant thereof, may be administered in the form of a peptide, or in the form of a nucleic acid encoding the peptide, for subsequent expression, e.g., in antigen presenting cells (APCs). If administering a nucleic acid encoding the nelipepimut-S, or variant thereof, the nucleic acid may be administered as naked DNA or RNA, or administered in a viral or non-viral vector. In some embodiments, the nelipepimut-S, or variant thereof (peptide or nucleic acid), is administered to the individual intra-dermally.

Introduction of the genetic sequence that encodes the NPS or variant thereof can be achieved by various means. The method may include administering to the individual a vector comprising a nucleotide sequence, which encodes an NPS or variant thereof (Tindle, R. W. et al., *Virology,* 1994, 200:54). In another embodiment, the method comprises administering to the subject naked nucleic acid (DNA or RNA) which encodes an NPS or variant thereof, or in another embodiment, two or more peptides of such peptides (Nabel, et al. *PNAS-USA,* 1990, 90: 11307). In another embodiment, multi-epitope, analogue-based cancer vaccines are utilized. Each possibility represents a separate embodiment of the present invention.

Nucleic acids (DNA or RNA) can be administered to an individual via any means as is known in the art, including intra-dermal, parenteral, or intravenous administration, or in another embodiment, by means of a gene gun. In another embodiment, the nucleic acids are administered in a composition, which correspond, in other embodiments, to any embodiment listed herein. DNA or RNA can be administered to an individual as a naked nucleic acid or carried by a vector.

Vectors for use according to methods of this invention can comprise, in another embodiment, any vector that facilitates or allows for the expression of a peptide (e.g., NPS peptide or a variant thereof) in an individual in vivo. The term "vector" is used to refer to any molecule (e.g., nucleic acid, plasmid, virus, particle) usable to transfer coding sequence information (e.g., nucleic acid sequence encoding NPS peptide or variant thereof) to a cell or individual. Nucleic acid vaccines for several cancers have entered clinical trials (Wahren B et al., "DNA Vaccines: Recent Developments and the Future," *Vaccines,* 2014, 2:785-796; Fioretti D. et al., "DNA Vaccines: Developing New Strategies Against Cancer, *Journal of Biomedicine and Biotechnology,* 2010, 2010 (938):174378).

In one embodiment, the vector is a viral vector. In another embodiment, the vector is a non-viral vector. In one embodiment the non-viral vector is a nucleic acid vector such as plasmid DNA or mRNA vector (see, for example, Weide B. et al., "Plasmid DNA- and messenger RNA-based Anti-Cancer Vaccination," *Immunol Lett,* 2008, 115(1):33-42); Kim H. et al., "Self-Assembled Messenger RNA Nanoparticles (mRNA-NPs) for Efficient Gene Expression," *Sci Rep,* 2015, 5:12737); Ulmer J. B. et al., "RNA-based Vaccines", Vaccine, 2012, 30:4414-4418). In another embodiment, "vectors" includes attenuated viruses, such as vaccinia or fowlpox, such as described in, e.g., U.S. Pat. No. 4,722,848, incorporated herein by reference. In another embodiment, the vector is BCG (Bacille Calmette Guerin), such as described in Stover et al., *Nature,* 1991, 351:456-460.

Other vectors useful for therapeutic administration or immunization of the NPS peptide or variant peptides, e.g., *Salmonella typhi* vectors, *Listeria monocytogenes* vectors, and the like, will be apparent to those skilled in the art from the description herein. Non-limiting examples of vectors that may be used to administer nucleic acid molecules to subjects in vivo and cells in vitro include adenovirus, adeno-associated virus, retrovirus (e.g., Moloney murine leukemia virus (MoMLV)), lentivirus, pox virus (e.g., vaccinia virus, Modified vaccinia Ankara (MVA)), herpes virus (e.g., cytomegalovirus), sendai virus, virus-like particles (VLPs), plasmids, cationic lipids, liposomes, and nanoparticles.

A "coding sequence" is a nucleic acid sequence that is transcribed into mRNA and/or translated into a polypeptide. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences. Variants or analogs may be prepared by the deletion of a portion of the coding sequence, by insertion of a sequence, and/or by substitution of one or more nucleotides within the sequence. Techniques for modifying nucleic acid sequences, such as site-directed mutagenesis, are well known to those skilled in the art (See, e.g., Sambrook et al., Molecular Cloning: A Laboratory Manual, Second Edition, 1989; DNA Cloning, Vols. I and II, D. N. Glover ed., 1985). Optionally, the nucleic acid sequences of the present invention, and composition and methods of the invention that utilize such polynucleotides, can include non-coding sequences.

The term "operably-linked" is used herein to refer to an arrangement of flanking control sequences wherein the flanking sequences so described are configured or assembled so as to perform their usual function. Thus, a flanking control sequence operably-linked to a coding sequence may be capable of effecting the replication, transcription and/or translation of the coding sequence under conditions compatible with the control sequences. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleic acid sequence coding for a peptide (e.g., a NPS peptide or variant NPS peptide) will typically have its own operably-linked promoter sequence.

In another embodiment, the vector further encodes for an immunomodulatory compound, as described herein. In another embodiment, the individual is administered an additional vector encoding same, concurrent, prior to or following administration of the vector encoding an NPS peptide or variant peptide to the individual.

Optionally, the nelipepimut-S, or variant thereof, may be administered in the form of a fusion polypeptide, in which the nelipepimut-S or variant is directly or indirectly fused to another nelipepimut-S or variant amino acid sequence(s), or that of a different peptide(s). Optionally, a nucleic acid encoding the nelipepimut-S, or variant thereof, may be administered in the form of a genetic construct comprising nucleic acids encoding multiple copies of the nelipepimut-S or variant(s) amino acid sequence (as a multimer). Optionally, the genetic construct can include further nucleic acids encoding other peptides.

Preferably, the treatment includes administration of an immunologic adjuvant, such as GM-CSF, which can be administered with the nelipepimut-S, or variant thereof, within the same or separate formulations. The adjuvant may be administered to the individual by any effective method. In some embodiments, the adjuvant is administered intra-dermally.

The NPS or variant thereof can be administered with an immunologic adjuvant or combination of adjuvants. The immunogen or composition containing the NPS or variant thereof may be referred to herein as a vaccine, a peptide vaccine, and the like.

The adjuvant may be of any class such as alum salts and other mineral adjuvants, bacterial products or bacteria-derived adjuvants, tensoactive agents (e.g., saponins), oil-in-water (o/w) and water-in-oil (w/o) emulsions, liposome adjuvants, cytokines (e.g., IL-2, GM-CSF, IL-12, and IFN-gamma), and alpha-galactosylceramide analogs. Non-limiting examples of adjuvants include Montanide emulsions, QS21, Freund's complete or incomplete adjuvant, aluminum phosphate, aluminum hydroxide, *Bacillus* Calmette-Guerin (BCG), and alum. In one embodiment, the adjuvant is an agent that enhances the immune system's CTL response against the NPS or variant thereof. The adjuvant may be administered in the same composition as the NPS or variant thereof, or in the same composition as the one or more trastuzumab or derivative thereof, or in the same composition as both the NPS or variant thereof and the trastuzumab or derivative thereof, or in a composition separate from the NPS or variant thereof and trastuzumab or derivative thereof.

In some embodiments, the adjuvant is GM-CSF and a dose of 250 mcg of GM-CSF is administered per day. The adjuvant may be administered at intervals, such as every three weeks (q3wk). In some embodiments, 1,000 mcg of the nelipepimut-S or variant thereof, and 250 mcg of the GM-CSF, are administered intra-dermally every three weeks, 30-120 minutes after completion of infusion of trastuzumab or a derivative thereof.

Nelipepimut-S(NPS) comprises a HER2/neu peptide consisting of the amino acid sequence KIFGSLAFL (SEQ ID NO:1), and stimulates specific CD8+ CTLs following binding to specific HLA molecules on antigen presenting cells (APC). NPS and/or variants of NPS may be administered to the individual. NPS variants have one or more amino acid substitutions. Amino acids of NPS may be substituted with naturally occurring amino acids or modified amino acids. NPS variant peptides and their production are described in U.S. Pat. No. 8,802,618, which is incorporated herein by reference in its entirety. In some embodiments, the NPS variant has an alpha-aminobutyric acid, norvaline or norleucine at position 4 of SEQ ID NO:1, an alpha-aminobutyric acid, norvaline or norleucine at position 7 of SEQ ID NO:1, or an isophenylalanine at position 8 of SEQ ID NO:1. In some embodiments, the NPS variant is selected from among: K I F Abu S L A F L (SEQ ID NO:2); K I F Nva S L A F L (SEQ ID NO:3); K I F Nle S L A F L (SEQ ID NO:4); K I F G S L Abu F L (SEQ ID NO:5); K I F G S L Nva F L (SEQ ID NO:6); K I F G S L Nle F L (SEQ ID NO:7); and K I F G S L A isoF L (SEQ ID NO:8). NPS and NPS variants may be produced by methods known in the art.

Thus, the peptide may be synthetic, recombinantly produced, or purified from a known source.

Trastuzumab is a recombinant IgG1 kappa, humanized monoclonal antibody that selectively binds with high affinity to the extracellular domain of the human epidermal growth factor receptor protein (HER2). Trastuzumab is described in U.S. Pat. No. 5,821,337, which is incorporated herein by reference in its entirety. The amino acid sequences of the light and heavy chains of trastuzumab are set forth in SEQ ID NO:9 and SEQ ID NO:10.

The amino acid sequence of the light chain of trastuzumab:

```
                                         (SEQ ID NO: 9)
DIQMTQSPSS LSASVGDRVT ITCRASQDVN TAVAWYQQKP

GKAPKLLIYS ASFLYSGVPS RFSGSRSGTD FTLTISSLQP

EDFATYYCQQ HYTTPPTFGQ GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC.
```

The amino acid sequence of the heavy chain of trastuzumab:

```
                                         (SEQ ID NO: 10)
EVQLVESGGG LVQPGGSLRL SCAASGFNIK DTYIHWVRQA

PGKGLEWVAR IYPTNGYTRY ADSVKGRFTI SADTSKNTAY

LQMNSLRAED TAVYYCSRWG GDGFYAMDYW GQGTLVTVSS

ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSCDKTHTCP PCPAPELLGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSREE

MTKNQVSLTC LVKGFYPSDI AVEWESNGQP ENNYKTTPPV

LDSDGSFFLY SKLTVDKSRW QQGNVFSCSV MHEALHNHYT

QKSLSLSPG.
```

In some embodiments of the various embodiments of methods and compositions herein, trastuzumab-anns (Kanjinti™, Amgen and Allergan), trastuzumab-qyyp (Trazimera™, Pfizer), trastuzumab-dttb (Ontruzant™, Samsung Bioepis), trastuzumab-pkrb (Herzuma™, Celltrion), trastuzumab-dkst (Ogivri™, Mylan GmbH), or a derivative of any of the foregoing is administered.

Optionally, in the various embodiments of methods and compositions herein, a trastuzumab derivative may be used in place of trastuzumab. The derivative of trastuzumab, if used, retains the binding specificity for the extracellular domain of HER2. Preferably, the trastuzumab selectively binds to HER2 with high affinity in a cell-based assay (e.g., Kd≤5 nM).

Examples of trastuzumab derivatives include, but are not limited to, those listed in Tables 1 and 2 of Selis F. et al., *Int J Mol Sci.*, 2016 April; 17(4): 491, which is incorporated herein by reference in its entirety (e.g., TrastFab, TrastF(ab')2, TrastFab', TrastFab'-Cys-PEG(2×10 kDa), TrastFab'-Cys-PEG(2×20 kDa), and TrastFab-(N-Term)-PEG20 kDa). The trastuzumab or trastuzumab derivative may be modified or unmodified, and may be conjugated or unconjugated.

Fragments and variants of a peptide such as NPS or an antibody such trastuzumab can be generated and tested for the presence of immunogenic activity or affinity for its target using standard techniques known in the art. Polynucleotides, peptides, chimeric, and conjugated polypeptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990) (Karlin, S. and Altschul, S. F. (1990) "Methods for Assessing the Statistical Significance of Molecular Sequence Features by Using General Scoring Schemes," *Proc. Natl. Acad. Sci. USA* 87:2264-2268), modified as in Karlin and Altschul (1993) (Karlin, S. and Altschul, S. F. (1993) "Applications and Statistics for Multiple High-Scoring Segments in Molecular Sequences," *Proc. Natl. Acad. Sci. USA* 90:5873-5877. Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See Worldwide Website: ncbi.nlm.nih.gov.

In some embodiments, the trastuzumab derivative comprises a light chain and heavy chain with at least 60%, 65%, 70%, 75%, 80%, 85%, 90%, 95%, 96%, 97%, 98%, 99%, or 100% sequence identity with SEQ ID NO:9 and/or SEQ ID NO:10, respectively.

The derivative of trastuzumab may be a whole antibody, or antigen-binding fragment thereof, such as a mono-clonal antibody, humanized antibody, chimeric antibody, minibody, bifunctional antibody, single chain antibody (scFv), variable region fragment (Fv or Fd), Fab or F(ab)2. In some embodiments, the derivative of trastuzumab is ado-trastuzumab emtansine (see WO/2001/000244, which is incorporated herein by reference in its entirety).

Preferably, booster doses of NPS and/or an NPS variant are employed. In some embodiments, the administration of the NPS or variant thereof represents a primary vaccination phase, and wherein the method further comprises, after completion of the primary vaccination, administering 1, 2, 3, 4, or more booster doses of NPS or variant thereof for a period of up to 30 months or longer, optionally with an immunologic adjuvant (e.g., GM-CSF), at a lesser frequency than the primary vaccination.

In some embodiments, two or more booster doses of NPS or variant thereof are administered, and wherein one booster dose is administered every 6 months. Each booster dose may be the same amount of NPS and/or NPS variant as delivered in primary doses, or may be a different amount (more or less).

One or more additional therapeutic agents may be administered to the individual before, during, or after administration of the trastuzumab and the nelipepimut-S or variant thereof. Additional therapeutic agents may include anticancer agents such as an immunotherapeutic agent, a targeted agent, or chemotherapeutic agent. In some embodiments, an immune checkpoint inhibitor is administered.

The additional therapeutic agents may be administered by any route suitable for the function of the agent used, such as intravenously, intramuscularly, subcutaneously, topically, orally, transdermally, intradermally, intraperitoneally, intraorbitally, by implantation, by inhalation, intrathecally, intraventricularly, or intranasally.

In some embodiments of the various methods of the invention, the additional therapeutic to be administered to the individual is an immunotherapy. As used herein, the term "immunotherapy" refers to the treatment of disease via the stimulation, induction, subversion, mimicry, enhancement, augmentation or any other modulation of a subject's immune system to elicit or amplify adaptive or innate immunity (actively or passively) against cancerous or otherwise harmful proteins, cells or tissues. Immunotherapies (i.e., immunotherapeutic agents) include cancer vaccines, immunomodulators, checkpoint inhibitors, tumor microenvironment modulators, monoclonal antibodies (e.g., humanized monoclonal antibodies)—including bispecific antibodies, immunostimulants, dendritic cells, and viral therapies, whether designed to treat existing cancers or prevent the development of cancers or for use in the adjuvant setting to reduce likelihood of recurrence of cancer.

The additional therapeutic agent may be an immunotherapy, i.e., an immunotherapeutic agent. For example, the immunotherapy may be a checkpoint inhibitor (also known as an immune checkpoint inhibitor), which is a compound or agent that blocks or inhibits immune checkpoint proteins (i.e., that blocks or inhibits checkpoint receptors or checkpoint receptor ligands). Non-limiting examples of compounds or agents that are checkpoint inhibitors, or compounds or agents that are able to modulate the activity of checkpoint inhibitors, which may be used, include small molecules, peptides, and antibodies. Non-limiting examples of antibodies include nivolumab (OPDIVO), pembrolizumab (KEYTRUDA), pidilizumab (CT-011), MEDI0680 (AMP-514), AMP-224, AUNP-12, BMS 936559, atezolizumab (MPDL3280A), durvalumab (MEDI4736), avelumab (MSB0010718C), BMS935559 (MDX-1105), rHIgM12B7, BMS-986016, GSK2831781, IMP321, lirilumab (BMS-986015), IPH2101 (1-7F9), PF-05082566, Urelumab (BMS-663513), and MEDI6469, whereas non-limiting examples of small molecules include Indoximod (NLG 9189), NLG 919, and epacadostat (INCB024360).

Examples of checkpoint proteins that may be targets for modulation include, but are not limited to, CTLA-4, PD-L1, PD-L2, PD1, B7-H3, B7-H4, BTLA, HVEM, TIM3, GAL9, LAG3, VISTA, IDO, KIR, 2B4 (belongs to the CD2 family of molecules and is expressed on all NK cells, and memory CD8$^+$ T cells), CD160 (also referred to as BY55), CGEN-15049, CHK 1 and CHK2 kinases, A2aR, and various B-7 family ligands. The negative immunoregulatory human cell surface receptor programmed death-1 (PD-1) is a member of the immunoglobulin superfamily (IGSF) of molecules involved in regulation of T cell activation. PD-1 acquired its name 'programmed death' when it was identified in 1992 as a gene upregulated in T cell hybridoma undergoing cell death. The structure of PD-1 is composed of one IGSF domain, a transmembrane domain, and an intracellular domain containing an immunoreceptor tyrosine-based inhibitory motif (ITIM) and an immunoreceptor tyrosine-based switch motif (ITSM). PD-1 has two binding partners: PD-L1 (B7-H1, CD274) and PD-L2 (B7-DC, CD273). PD-L1 is expressed broadly on both hematopoietic and non-hematopoietic lineages. It is found on T cell, B cells, macrophages, NK cells, DCs, and mast cells as well as in peripheral tissues. PD-1 engagement represents one means by which tumors evade immunosurveillance and clearance. Blockade of the PD-1 pathway has been demonstrated by nivolumab.

The additional therapeutic agent may be a chemotherapeutic agent, such as one or more of capecitabine, carboplatin, cisplatin, cyclophosphamide, docetaxel, doxorubicin (liposomal or non-liposomal), epirubicin, eribulion, 5-Fluorouracil (5FU), gemcitabine, ixabepiline, methotrexate, paclitaxel (albumin-bound or non-albumin-bound), and vinorelbine. A combination of chemotherapeutic agents may be administered, such as doxorubicin and cyclophosphamide; or doxorubicin and cyclophosphamide followed by paclitaxel or docetaxel; or doxetaxel, doxorubicin, and cyclophosphamide; or cyclophosphamide and docetaxel; or cyclophosphamide, methotrexate, and 5-FU (CMF); or 5-FU, doxorubicin, and cyclophosphamide (FAC); or 5-FU, epirubicin, and cyclophosphamide (FEC); docetaxel, carboplatin, and trastuzumab; or docetaxel, carboplatin, trastuzumab, and pertuzumab; or paclitaxel and trastuzumab; or paclitaxel, trastuzumab, and pertuzumab.

In some embodiments, the nelipepimut-S, or variant thereof, trastuzumab, or derivative thereof, immunologic adjuvant (if used), and additional therapeutic agent (if used) are administered intravenously, intramuscularly, subcutaneously, topically, orally, transdermally, intradermally, intraperitoneally, intraorbitally, by implantation, by inhalation, intrathecally, intraventricularly, or intranasally.

In some embodiments, the trastuzumab, or derivative thereof, is administered intravenously, and the nelipepimut-S, or variant thereof, is administered intradermally. In some embodiments, the NPS, or variant thereof, and immunologic adjuvant are administered intradermally, and the trastuzumab or derivative thereof is administered intravenously.

In some embodiments, the individual has had TNBC and, after receiving therapy for the TNBC (such as standard of care treatment), is clinically disease-free at the time of administration of the TZ, or derivative thereof, and NPS or variant thereof, and the method of the invention delays or prevents recurrence of the TNBC in the individual.

The methods of the invention can reduce tumor size and/or increases the individual's disease-free survival (relapse-free survival). In some embodiments, the trastuzumab and the nelipepimut-S, or variant thereof, have a synergistic effect on the individual.

Other aspects of the invention concern medicaments and kits useful for treating TNBC and/or for inducing an immune response to HER2/neu in an individual with a TNBC expressing low levels of HER2/neu, such as in the methods of the invention. One aspect of the invention concerns a medicament comprising nelipepimut-S, or variant thereof, for use in combination with trastuzumab for treating triple-negative breast cancer in an individual. The medicament may further include an immunologic adjuvant, such as GM-CSF.

Another aspect of the invention concerns a medicament comprising trastuzumab, for use in combination with nelipepimut-S, or variant thereof, for treating triple-negative breast cancer in an individual.

Another aspect of the invention is a kit that comprises a first container, a second container and a package insert, wherein the first container comprises at least one dose of a medicament comprising trastuzumab, the second container comprises at least one dose of a medicament comprising nelipepimut-S, or variant thereof, and the package insert comprises instructions for treating an individual for triple-negative breast cancer using the medicaments. The kit may further include an immunologic adjuvant, such as GM-CSF. The immunologic adjuvant can be held in the container with the nelipepimut-S, or variant thereof, or in a separate container. Kits can include additional therapeutic agents (i.e., in addition to trastuzumab or trastuzumab derivative, and NPS or NPS variant).

The kits preferably include packaging material. As used herein, the term "packaging material" refers to a physical structure housing the components of the kit. The packaging material can maintain the components in a sterile state, and can be made of material commonly used for such purposes (e.g., paper, corrugated fiber, glass, plastic, foil, ampules, etc.). The label or packaging insert can include appropriate printed and/or digital instructions, for example, for practicing a method of the invention, e.g., treating triple-negative breast cancer (TNBC). Thus, in additional embodiments, a kit includes a label or packaging insert including instructions for practicing a method of the invention in solution.

Instructions can therefore include instructions for practicing any of the methods of the invention described herein. For example, pharmaceutical compositions can be included in a container, pack, or dispenser together with instructions for administration to a subject to treat TNBC (e.g., TNBC expressing low levels of HER2/neu). Instructions may additionally include indications of a satisfactory clinical endpoint or any adverse symptoms that may occur, storage information, expiration date, or any information required by regulatory agencies such as the Food and Drug Administration or European Medicines Agency for use in an individual.

The instructions may be digital or on "printed matter," e.g., on paper or cardboard within the kit, on a label affixed to the kit or packaging material, or attached to a vial or tube containing a component of the kit. Instructions may comprise voice or video tape and additionally be included on a computer readable medium, such as a disk (diskette or hard disk), optical CD such as CD- or DVD-ROM/RAM, magnetic tape, electrical storage media such as RAM and ROM and hybrids of these such as magnetic/optical storage media.

Kits can additionally include a buffering agent, a preservative, or an agent for stabilizing at least one compound used in the methods of the invention. Each component of the kit can be enclosed within an individual container or in a mixture and all of the various containers can be within single or multiple packages.

Kits can include packaging material that is compartmentalized to receive one or more containers such as vials, tubes, and the like, each of the container(s) including one of the separate elements to be used in a method described herein. Packaging materials for use in packaging pharmaceutical products include, by way of example only U.S. Pat. Nos. 5,323,907, 5,052,558 and 5,033,252. Examples of pharmaceutical packaging materials include, but are not limited to, blister packs, bottles, tubes, pumps, bags, vials, light-tight sealed containers, syringes, bottles, and any packaging material suitable for a selected formulation and intended mode of administration and treatment.

A kit may include one or more additional containers, each with one or more of various materials desirable from a commercial and user standpoint for use of the compounds used for treating TNBC and/or inducing the desired immune response. Non-limiting examples of such materials include, but not limited to, buffers, diluents, carrier, package, container, vial and/or tube labels listing contents and/or instructions for use, and package inserts with instructions for use.

A label can be on or associated with a container containing a compound used in the methods of the invention. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In some embodiments of the kit, the compound(s) used in the methods invention can be presented in a pack or dispenser device which can contain one or more unit dosage forms containing a compound disclosed herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

Compounds, and compositions comprising them, useful in the methods of the subject invention can be formulated according to known methods for preparing pharmaceutically useful compositions. Each of the trastuzumab, trastuzumab derivative, NPS, NPS variant, immunologic adjuvant, and additional therapeutic agents may be administered in combination with a carrier, diluent or excipient. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of at least one compound of the invention is combined with a suitable carrier or diluent in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptides and polynucleotides include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the compounds of the invention can also comprise suspension agents, protectants, lubricants, buffers, preservatives, and stabilizers.

In the study disclosed in Examples 1 and 2, Materials & Methods, and Figures herein, the investigators assessed the ability of the combination of Herceptin® antibody (trastuzumab) and NeuVax™ vaccine (HER2 protein E75 peptide administered with the immunoadjuvant GM-CSF) given in the adjuvant setting to prevent recurrences in NP (or NN if negative for both estrogen (ER) and progesterone (PR) receptors) breast cancer patients with tumors that express low (1+) or intermediate (2+) levels of HER2. Enrolled patients were randomized to receive trastuzumab and NeuVax™ vaccine or trastuzumab with GM-CSF alone (no NeuVax™ vaccine). The safety of the combination therapy was documented, specifically to ensure that no additive cardiac toxicity results from combination HER2-directed therapy. Efficacy has been documented by comparing the DFS and immunological responses between treatment groups. The primary efficacy endpoint is to compare DFS at 24 months between treatment groups. The primary safety issue is to prove there is no additive cardiac toxicity with combination HER2-directed therapy. A secondary endpoint of the trial is to compare DFS at 36 months. Immunologic responses to the vaccine were also documented and correlated to clinical benefit.

The study is a multi-center, prospective, randomized, single-blinded, placebo-controlled Phase II trial of Herceptin® antibody+NeuVax™ vaccine versus Herceptin® antibody+GM-CSF alone. The target study population is NP (or NN if negative for both ER and PR) breast cancer patients with HER2 1+ and 2+ expressing tumors who are disease-free after standard of care therapy. Disease-free subjects after standard of care multi-modality therapy were screened and HLA-typed. Nelipepimut-S (formerly called E75 peptide) is a CD8-eliciting peptide vaccine that is restricted to HLA-A2+ or HLA-A3+ patients (approximately two-thirds of the US population), and has been extended to HLA-A24+ and HLA-A26+ as well.

HLA-A2+/A3+/A24+/or A26+ patients who meet all other eligibility criteria were randomized to receive trastuzumab+NeuVax™ vaccine or trastuzumab+GM-CSF alone. For both groups, trastuzumab was given every three weeks as monotherapy for one year, and was given upon completion of standard of care chemotherapy/radiotherapy. The first trastuzumab infusion was given no sooner than three weeks and no later than 12 weeks after completion of chemotherapy/radiotherapy. Trastuzumab was dosed at the recommended initial loading dose of 8 mg/kg and at recommended maintenance doses of 6 mg/kg q3wk. Trastuzumab was administered as described in Section 4.3. Patients randomized to the NeuVax vaccine arm received vaccinations of nelipepimut-S peptide (1000 mcg) and GM-CSF (250 mcg) administered intradermally every three weeks for six total vaccinations, 30-120 minutes after completion of trastuzumab infusion. The NeuVax vaccine series will begin immediately after completion of the third trastuzumab infusion. In extenuating circumstances, the first vaccination may be delayed to the fourth or fifth trastuzumab infusion with prior approval from the Principal Investigator. Those patients randomized to the GM-CSF alone arm received vaccinations of GM-CSF (250 mcg) administered in an identical manner to those receiving NeuVax vaccine. Patients were blinded as to whether they are receiving NeuVax vaccine or GM-CSF alone.

Upon completion of the vaccination series, booster inoculations (same dose and route) were administered every six months×4 for total combination (trastuzumab and NPS vaccine) treatment duration of 30 months. The first booster inoculation occurred with the final trastuzumab infusion, with subsequent boosters timed every six months from the first booster. Booster inoculations occur for patients randomized to receive nelipepimut-S/GM-CSF, as well as patients randomized to receive GM-CSF alone, and consisted of the same treatment drugs and dosing (i.e., nelipepimut-S/GM-CSF patients were boosted with nelipepimut-S/GM-CSF, while GM-CSF alone patients were boosted with GM-CSF alone). Blinding was maintained throughout the study in patients, clinical personnel (clinician M.D.s, nursing and ancillary personnel), as well as clinical study coordinators, data managers, statisticians, and the clinical research organization's leadership, with the exception of the research pharmacists who were preparing the doses and labeling of the blinded material.

Subjects have been followed for safety issues, immunologic response and clinical recurrence. Patients are monitored 48-72 hours after each inoculation for reaction to the inoculation as well as documentation of any adverse effects experienced. Immunologic response was in vivo delayed type hypersensitivity (DTH) reactions, and will be also documented with in vitro phenotypic and functional assays. All patients were initially intended to be followed for a total of 36 months to document disease-free status.

Definitions

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

After setting forth the invention in detail, it may be helpful to the understanding thereof to define several terms, and these are accordingly set forth in the next section, below. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The term "polynucleotide" or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR 2 ("amidate"), P(O)R, P(O)OR', CO or CH 2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "expression" as used herein refers to production of mRNA as well as to the translation of mRNA into protein.

As used herein, the terms "polypeptide", "peptide", and "protein" are used interchangeably to refer to polymers of any length comprising amino acid residues linked by peptide bond.

The terminology used herein is for the purpose of describing particular embodiments only and is not intended to be limiting of the invention. As used herein, the indefinite articles "a", "an" and "the" should be understood to include plural reference unless the context clearly indicates otherwise.

As used herein, the terms "including", "includes", "having", "has", "with", or variants thereof, are intended to be inclusive similar to the term "comprising".

As used herein, the terms "individual", "subject", and "patient" are interchangeable and refer to a human of any gender capable of being inflicted with triple negative breast cancer. In some embodiments, the individual is a female 18 years of age or older. In some embodiments, the subject has, or has had, HER2 low-expressing (IHC1+/2+, FISH non-amplified) breast cancer.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, "treatment" refers to clinical intervention in an attempt to alter the natural course of the individual or cell being treated, and can be performed before or during the course of clinical pathology. Desirable effects of treatment include delaying or preventing the occurrence or recurrence of a disease or a condition, such as triple negative breast cancer, or symptom thereof, delaying onset of the disease or condition, alleviating a condition or symptom of the disease, diminishing any direct or indirect pathological consequences of the disease, decreasing the rate of disease progression, ameliorating or palliating the disease state, achieving remission or improved prognosis, and increasing disease-free survival. In treating the TNBC, the combination of trastuzumab, or derivative thereof, and NPS, or variant thereof, are administered in a therapeutically effective amount.

By "effective amount" it is meant the quantity of the trastuzumab, or derivative thereof, and NPS, or variant thereof, that prevents or delays onset, prevents or delays recurrence, removes, reduces, or slows the deleterious effects of TNBC in humans. It is understood that the administered dose may be adapted by those skilled in the art according to the patient, the pathology, the mode of administration, etc.

As used herein, the term "tumor" refers to all neoplastic cell growth and proliferation, whether malignant or benign, and all pre-cancerous and cancerous cells and tissues. For example, a particular cancer may be characterized by a solid mass tumor or non-solid tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography) or magnetic resonance imaging (MRI), or by needle aspirations. The use of these latter techniques is more common in early detection. Molecular and phenotypic analysis of cancer cells within a tissue can usually be used to confirm if the cancer is endogenous to the tissue or if the lesion is due to metastasis from another site. Some tumors are unresectable (cannot be surgically removed due to, for example the number of metastatic foci or because it is in a surgical danger zone). The methods of the invention can be utilized for early, middle, or late stage disease, and acute or chronic disease.

MHC class I peptide vaccines are HLA-restricted but may bind to multiple HLA-types. HLA types have been associated with response to multiple immunotherapies to include checkpoint inhibitors. The relationships between HLA-type, predicted peptide binding potential, and clinical response have implications for the design and development of active immunotherapy. A randomized phase IIb trial is being conducted of the MHC class I peptide, E75 (HER2 369-377)+ GM-CSF (NeuVax)+trastuzumab versus GM-CSF+ trastuzumab to prevent recurrences in node positive and/or ER⁻/PR⁻ negative, HER2 low-expressing breast cancer patients. In a planned interim analysis, a significant disease-free survival benefit was demonstrated specifically in TNBC patients to NeuVax+trastuzumab. The analysis in Examples 1 and 2 examines the effect of HLA-type on trial outcomes.

Clinically disease-free, HER2 low-expressing (IHC1+/2+, FISH nonamplified), node positive (AJCC N1, N2, or N3) and/or triple negative breast cancer patients after standard therapy were tested for the presence of the A2, A3, A24, and A26 alleles by flow cytometry. HLA-A2, A3, A24, and/or A26+ patients were randomized to receive trastuzumab+NeuVax (vaccine group) or trastuzumab+GM-CSF (control group). All patients received one year of trastuzumab per standard of care. NeuVax or GM-CSF was given every three weeks×6 starting with the third trastuzumab dose, and then boosted every six months×4. The pre-specified interim analysis was triggered six months after last patient enrollment. The primary endpoint was disease free survival evaluated by log rank. The MHC Class I binding predictions were made using the IEDB Analysis Resource Consensus tool.

Materials and Methods

Experimental: Herceptin+NeuVax vaccine Study Arm. Patients randomized to this arm received Herceptin® antibody (trastuzumab) every 3 weeks as monotherapy for 1 year; the first trastuzumab infusion was given no sooner than 3 weeks and no later than 12 weeks after completion of standard of care chemotherapy/radiotherapy. Trastuzumab was dosed at the recommended initial loading dose of 8 mg/kg and at recommended maintenance doses of 6 mg/kg q3wk. Patients received vaccinations of NeuVax vaccine administered intradermally every 3 weeks for 6 total vaccinations, 30-120 minutes after completion of trastuzumab infusion. The NPS vaccine series began immediately after completion of the third trastuzumab infusion, but could have been delayed to the fourth or fifth trastuzumab infusion with prior approval from the PI. Patients were blinded regarding assigned arm. After completion of primary vaccine series, patients received 4 NeuVax vaccine booster inoculations administered every 6 months×4 for total treatment duration of 30 months.

Experimental: Active Comparator: Herceptin+GM-CSF Only Study Arm. Patients randomized to this arm received Herceptin® antibody (trastuzumab) every 3 weeks as monotherapy for 1 year. The first trastuzumab infusion was given no sooner than 3 weeks and no later than 12 weeks after completion of standard of care chemotherapy/radiotherapy. Trastuzumab was dosed at the recommended initial loading dose of 8 mg/kg and at recommended maintenance doses of 6 mg/kg q3wk. Patients received inoculations of GM-CSF only (250 mcg) administered intradermally every 3 weeks for 6 total inoculations, 30-120 minutes after completion of trastuzumab infusion. The GM-CSF only inoculation series begun immediately after completion of the third trastuzumab infusion. Patients were blinded as to whether they are receiving NeuVax vaccine or GM-CSF only. After completion of six-inoculation primary vaccine series, patients then received a total of four GM-CSF only booster inoculations to be administered at 12, 18, 24, and 30 months from the date of the first trastuzumab infusion.

Trastuzumab intervention. Trastuzumab was administered to patients every three weeks as monotherapy for one year, given upon completion of standard of care chemotherapy/radiotherapy. The first trastuzumab infusion was given no sooner than three weeks and no later than 12 weeks after completion of chemotherapy/radiotherapy. Trastuzumab was dosed at the recommended initial loading dose of 8 mg/kg and at recommended maintenance doses of 6 mg/kg q3wk.

Nelipepimut-S intervention. At the time of vaccine administration, a frozen solution of E75 acetate (1.5 mg/ml) was thawed and 1000 mcg E75 peptide (KIFGSLAFL (SEQ ID NO:1), HER2/neu, 369-377) mixed thoroughly with 250 mcg GM-CSF (sargramostim). This constituted the NeuVax vaccine. For patients randomized to the trastuzumab+NeuVax vaccine arm, they commenced trastuzumab monotherapy and then began the NeuVax vaccine series immediately after completion of the third trastuzumab infusion. The vaccine series consisted of NeuVax vaccine administered intradermally every three weeks for six total vaccinations, 30-120 minutes after completion of trastuzumab infusion.

GM-CSF intervention. For patients randomized to the trastuzumab+GM-CSF only arm, they commenced trastuzumab monotherapy and then began the GM-CSF (sargramostim) inoculation series immediately after completion of the third trastuzumab infusion. The GM-CSF inoculation series consisted of 250 mcg GM-CSF administered intradermally every three weeks for six total vaccinations, 30-120 minutes after completion of trastuzumab infusion.

Study Criteria: Inclusion Criteria.
Patients were included in the study based on the following criteria:
  Women 18 years or older
  Node-positive breast cancer (AJCC N1, N2, or N3)
  Node-negative breast cancer if negative for both estrogen (ER) and progesterone (PR) receptors and have received chemotherapy as standard of care
  Clinically cancer-free (no evidence of disease) after standard of care therapy (surgery, chemotherapy, radiation therapy as directed by NCCN guidelines). Hormonal therapy continued per standard of care. Neoadjuvant chemotherapy was allowed.
  Recovery from any toxicity(ies) associated with prior adjuvant therapy.
  HER2 expression of 1+ or 2+ by IHC. FISH (or Dual-ISH) testing must be performed on IHC 2+ tumors and shown to be non-amplified by FISH (≤2.0) (or by Dual-ISH, ≤2.0).
  HLA-A2, A3, A24, or A26 positive
  LVEF >50%, or an LVEF within the normal limits of the institution's specific testing (multigated acquisition [MUGA] cardiac scan or echocardiogram [Echo])
  Eastern Cooperative Oncology Group (ECOG) performance status of 0 or 1
  Signed informed consent Adequate birth control (abstinence, hysterectomy, bilateral oophorectomy, bilateral tubal ligation, oral contraception, intrauterine device (IUD), or use of condoms or diaphragms)

Must start study treatment (receive first trastuzumab infusion) between 3-12 weeks from completion of standard of care therapy.

Study Criteria: Exclusion Criteria.

Patients were excluded from the study based on the following criteria:

Node-negative breast cancer (American Joint Committee on Cancer [AJCC] N0 or N0(i+)) unless negative for both estrogen (ER) and progesterone (PR) receptors and has received chemotherapy as standard of care Clinical or radiographic evidence of distant or residual breast cancer HER2 negative (IHC 0) or HER2 3+ or FISH or Dual-ISH amplified (FISH >2.0; Dual-ISH >2.0)

Human leukocyte antigen (HLA) −A2, A3, A24, A26 negative

History of prior trastuzumab therapy

New York Heart Association (NYHA) stage 3 or 4 cardiac disease

Left ventricular ejection fraction (LVEF) <50%, or less than the normal limits of the institution's specific testing (MUGA or Echo)

Immune deficiency disease or HIV, HBV, HCV

Receiving immunosuppressive therapy including chemotherapy, chronic steroids, methotrexate, or other known immunosuppressive agents ECOG performance status ≥2

Total (serum) bilirubin >1.8 mg/dL, creatinine >2.0 mg/dL, hemoglobin <10 g/L, platelets <50,000/uL, WBC <2,000/uL Pregnancy (assessed by urine HCG)

Breast feeding

Any active autoimmune disease requiring treatment, with the exception of vitiligo Active pulmonary disease requiring medication to include multiple inhalers Involved in other experimental protocols (except with permission of the other study PI)

Assessment: Disease-free survival (DFS) at 24 months. DFS for all patients regardless of randomization was determined by patients' own physicians at the individual study sites during routine follow-up screening. This occurred every three months for the first 24 months after completion of primary therapies and every six months thereafter with clinical exam, and laboratory and radiographic surveillance. The primary objective of the study was disease-free survival (DFS) at 24 months.

Assessment: Disease-free survival (DFS) at 36 months. DFS for all patients regardless of randomization was determined by patients' own physicians at the individual study sites during routine follow-up screening. This occurred at months 30 and 36 after completion of primary therapies with clinical exam, and laboratory and radiographic surveillance. The secondary objective of the study was disease-free survival (DFS) at 36 months.

Assessment: Cardiac toxicity at 24 months. Each patient, regardless of randomization, underwent cardiac assessment (ejection fraction) at baseline Multiple Gated Acquisition scan (MUGA) preferred, echocardiogram (ECHO) allowed, consistency required) and at 3, 6, 12, and 24 months. Cardiac assessment continued every six months if a patient experienced a greater than 10% reduction from baseline for the duration of the trial or until resolution.

Local and systemic toxicities for duration of vaccine or inoculation series and booster series. Standard local and systemic toxicities were collected and graded per the National Cancer Institute Common Terminology Criteria for Adverse Events (NCI-CTCAE), version 4.03 toxicity scale. For both the regular and booster inoculations, patients were monitored closely for one hour after inoculation with questioning, serial exams and vital signs every 15 minutes to observe for a hypersensitivity reaction. Patients also returned to the clinic 48-72 hours after each inoculation for questioning regarding systemic toxicity and to examine and measure the local reaction at the inoculation sites.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Pre-Specified Interim Analysis of a Randomized Phase 2b Trial of Trastuzumab Plus Nelipepimut-S(NEUVAX) Versus Trastuzumab for the Prevention of Recurrence Demonstrates Benefit in Triple Negative (HER2 Low-Expressing) Breast Cancer Patients Human epidermal growth factor receptor 2 (HER2) low-expressing breast cancer (immunohistochemistry (IHC) 1-2+) are not eligible for treatment with adjuvant trastuzumab (TZ). NSABP B-47 confirmed trastuzumab does not improve outcomes in HER2 low-expressing breast cancer (Fehrenbacher et al., *SABCS,* 2017, Abstract GS1-02). These patients are currently ineligible for HER2-directed therapy. TZ is among the most well-recognized examples of successful targeted therapy for cancer. 15-20% of BC patients are eligible to receive TZ as they are HER2 overexpressing (IHC3+ or FISH amplified).

Efforts to expand application of trastuzumab have been previously undertaken. The NSABP B-47 trial recently confirmed that TZ does not improve outcomes in this population (Fehrenbacher et al., 2017). HER2 negative, ER positive patients do very well and likely not in need of targeted therapy other than hormonal therapy; however, TNBC patients have the worst long term survival and have few treatment options. Therefore, there is a need for novel therapies for TNBC patients.

HER2 is also the target for trastuzumab, which 20% of breast cancer patients are eligible to receive. NeuVax is a HER2-targeting vaccine that initially was poised to be available to a broader base of 50-60% of breast cancer patients, whose tumors are HER2 "low expressing." As shown in FIG. 1, nelipepimut-S is the immunodominant peptide derived from the extracellular domain of the HER2 protein, a promising target for vaccination in patients with breast cancer. Nelipepimut-S stimulates specific CD8+ CTLs following binding to specific HLA molecules on antigen presenting cells (APC).

Phase 1/2 trials of adjuvant nelipepimut-S+GM-CSF (NeuVax) demonstrated a safe and immunogenic profile, and suggested clinical efficacy (Gall et al., *Cancer Res.,* 2017, 77:5374-83). The goal in employing this vaccine is to prime the immune system to recognize and attack HER2 protein found in breast cancer; consequently, when/if a patient with early-stage breast cancer is at risk for recurrence after completion of their front-line therapy, their immune system will recognize HER2 after nelipepimut-S administration and take action, thus delaying or preventing the clinical emergence of a relapse. This should be translated in the clinic as a prolongation of disease-free survival (DFS), and eventually overall survival (OS).

A multi-center, prospective, randomized, single-blinded, placebo-controlled Phase II trial of Herceptin® antibody+ NeuVax™ vaccine (nelipepimut-S(NPS, also known as E75 peptide) plus granulocyte macrophage-colony stimulating factor (GM-CSF)) versus Herceptin® antibody+GM-CSF alone was carried out. The target study population was node-positive (NP) (or node-negative [NN] if negative for both ER and PR) breast cancer patients with HER2 1+ and 2+ expressing tumors who were disease-free after standard of care therapy. Disease-free subjects after standard of care multi-modality therapy were screened and HLA-typed. The NeuVax™ vaccine is a CD8-eliciting peptide vaccine that was restricted to HLA-A2+ or HLA-A3+ patients (approximately two-thirds of the United States population), and has been extended to HLA-A24+ and HLA-A26+ as well. The study design is shown in FIG. 2.

Key Inclusion Criteria:
  Women ≥18 years
  High risk invasive breast cancer with HER2 expression of 1-2+ by IHC
  Clinically disease-free after receiving standard of care therapies
  HLA-A2, A3, A24, or A26 positive Assessments:
  Local and systemic toxicity
  Cardiac toxicity
  Immunologic in vivo response
  Disease Free Survival Detailed Inclusion Criteria:
  Women ≥18 years; ECOG PS 0-1
  Histologically proven invasive breast cancer that was node-positive (HR+/−) or node-negative (HR−) with HER2 expression of 1-2+ by IHC*
    For IHC 2+ tumors, FISH or Dual-ish HER2: CEP17≤2.0 (nonamplified)
  Clinically disease-free after receiving surgery, adjuvant or neoadjuvant chemotherapy and radiation
  HLA-A2, A3, A24, or A26 positive
  Patients who are HR− and HER2 1+/2+ are currently defined as TNBC patients Detailed Assessments:
  Local and systemic toxicity (NCI CTCAE version 4.03)
  Cardiac toxicity: cardiac ejection fraction (MUGA or echocardiography): baseline, 3, 6, 12, and 24 months
  Delayed type hypersensitivity (DTH) reaction (sensitive ball point pen method): pre-inoculation and post-inoculation time points
  DFS: recurrence assessed every 3 months for the first 24 months after completion of primary therapies and every 6 months thereafter
  Abbreviations: CEP, chromosome enumeration probe; DFS, disease-free survival; DTH, Delayed type hypersensitivity; ECOG PS, Eastern Cooperative Oncology Group performance status; FISH, fluorescent in situ hybridization; HER2, human epidermal growth factor receptor 2; HLA, human leukocyte antigen; HR, hormone receptor; IHC, immunohistochemistry; MUGA, multi-gated acquisition scan; NCI CTCAE, National Cancer Institute Common Terminology Criteria for Adverse Events.

Results from pre-specified interim analysis were obtained.
  6 months after the last patient was enrolled
  Safety and efficacy were assessed
Tables 1 and 2, below, show Patient Demographics (ITT)

TABLE 1

| Characteristics | NeuVax + TZ (N = 136) | TZ (N = 139) | p value |
|---|---|---|---|
| Age, years | 52.2 | 50.5 | 0.38 |
| Median (IQR) | (43.7-60.8) | (42.0-59.0) | |
| Race, n (%) | | | |
| White | 109 (80) | 97 (70) | 0.20 |
| Non-white | 25 (18) | 38 (27) | |
| Unknown | 2 (2) | 4 (3) | |
| Chemotherapy | | | |
| Adjuvant | 59 (43) | 57 (41) | 0.904 |
| Neoadjuvant | 72 (53) | 76 (55) | |
| None | 5 (4) | 6 (4) | |
| Clinical NeoAdj stage, n (%) | | | |
| 0 | 0 (0) | 1 (1) | |
| I | 4 (6) | 3 (4) | |
| II | 35 (49) | 31 (40) | 0.334 |
| III | 31 (43) | 40 (52) | |
| IV | 1 (1) | 0 (0) | |
| Unknown | 1 (1) | 2 (3) | |
| Path NeoAdj stage, n (%) | | | |
| 0 | 5 (7) | 4 (5) | 0.757 |
| I | 11 (15) | 9 (12) | |
| II | 28 (39) | 26 (34) | |
| III | 27 (38) | 37 (49) | |
| Unknown | 1 (1) | 0 (0) | |

TABLE 2

| Characteristics | NeuVax + TZ (N = 136) | TZ (N = 139) | p value |
|---|---|---|---|
| Path (no NeoAdj) stage, n (%) | | | |
| I | 10 (16) | 9 (14) | 0.985 |
| II | 26 (41) | 26 (41) | |
| III | 28 (44) | 28 (45) | |
| ER status | | | |
| Positive | 81 (60) | 94 (68) | 0.164 |
| Negative | 55 (40) | 45 (32) | |
| PR status | | | |
| Positive | 77 (57) | 82 (59) | 0.69 |
| Negative | 59 (43) | 57 (41) | |
| Surgery | | | |
| Yes | 136 (100) | 138 (99) | 0.638 |
| No | 0 | 1 (1) | |
| Radiotherapy | | | |
| Adjuvant | 109 (80) | 122 (88) | 0.092 |
| Neoadjuvant | 8 (6) | 2 (1) | |
| None | 19 (14) | 15 (11) | |
| Hormone therapy | | | |
| Yes | 73 (54) | 83 (60) | 0.248 |
| No | 61 (45) | 51 (37) | |
| Other | 2 (1) | 5 (4) | |

589 patients were screened and consented to HLA typing, only 16.6% were not eligible based on HLA status. 216 were appropriate HLA type, but screen failure or patient choice did not enroll. 275 patients enrolled. There were no clinicopathologic differences between treatment arms (AJCC7 stages).

Figure 3:
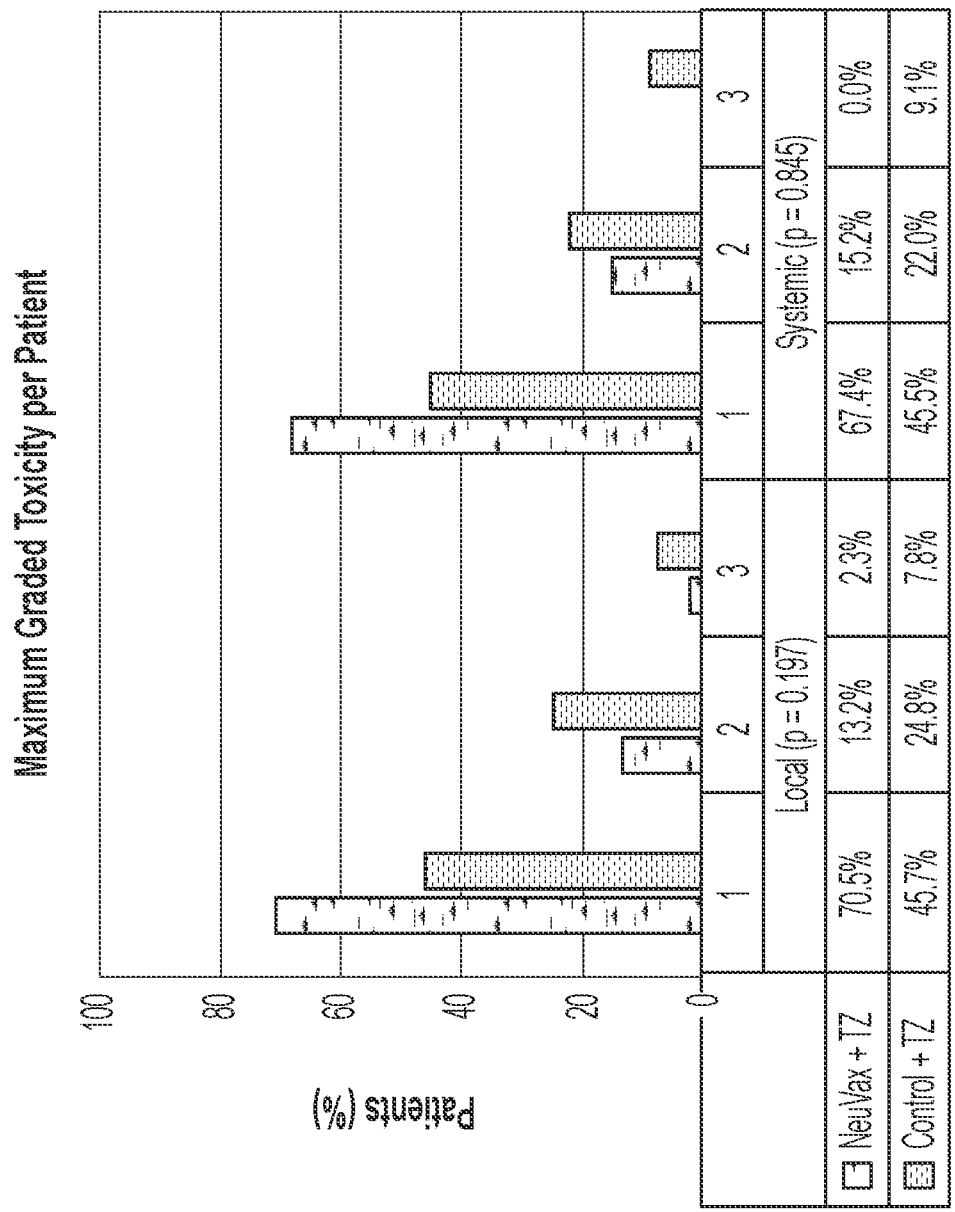
FIG. 3 shows a bar graph of treatment-related adverse events. 93.1% (243/261) of patients that received an intervention experienced at least 1 TRAE. There was no difference in TRAE between groups. The majority of TRAEs were grade 1 or 2, including local injection site reactions, skin induration, pruritus and fatigue. TRAE, treatment-related adverse event; TZ, trastuzumab.
Figure 4:
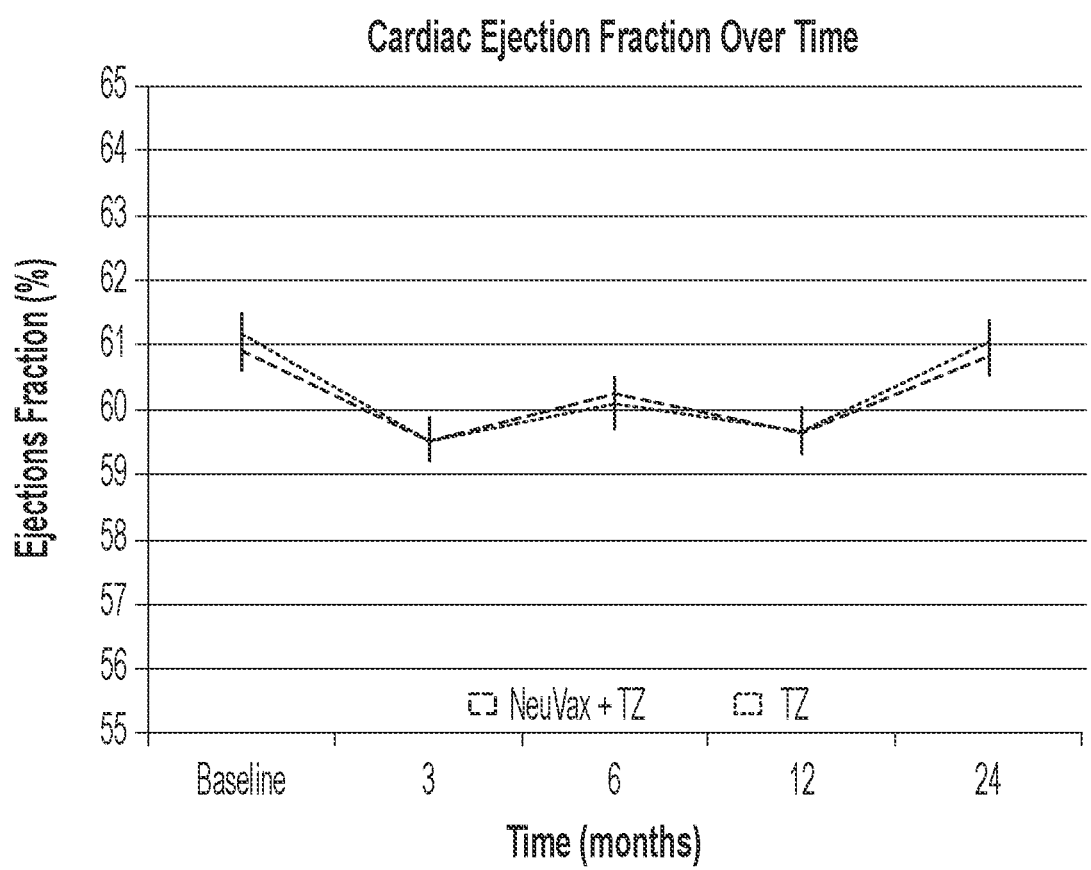
FIG. 4 shows a line graph of cardiac toxicity. There was no difference between treatment arms in cardiac ejection fraction over time (p=0.558) and at each time point. The addition of NeuVax™ vaccine to trastuzumab did not result in any additional cardiotoxicity compared with trastuzumab alone. TZ, trastuzumab.
Figure 5:
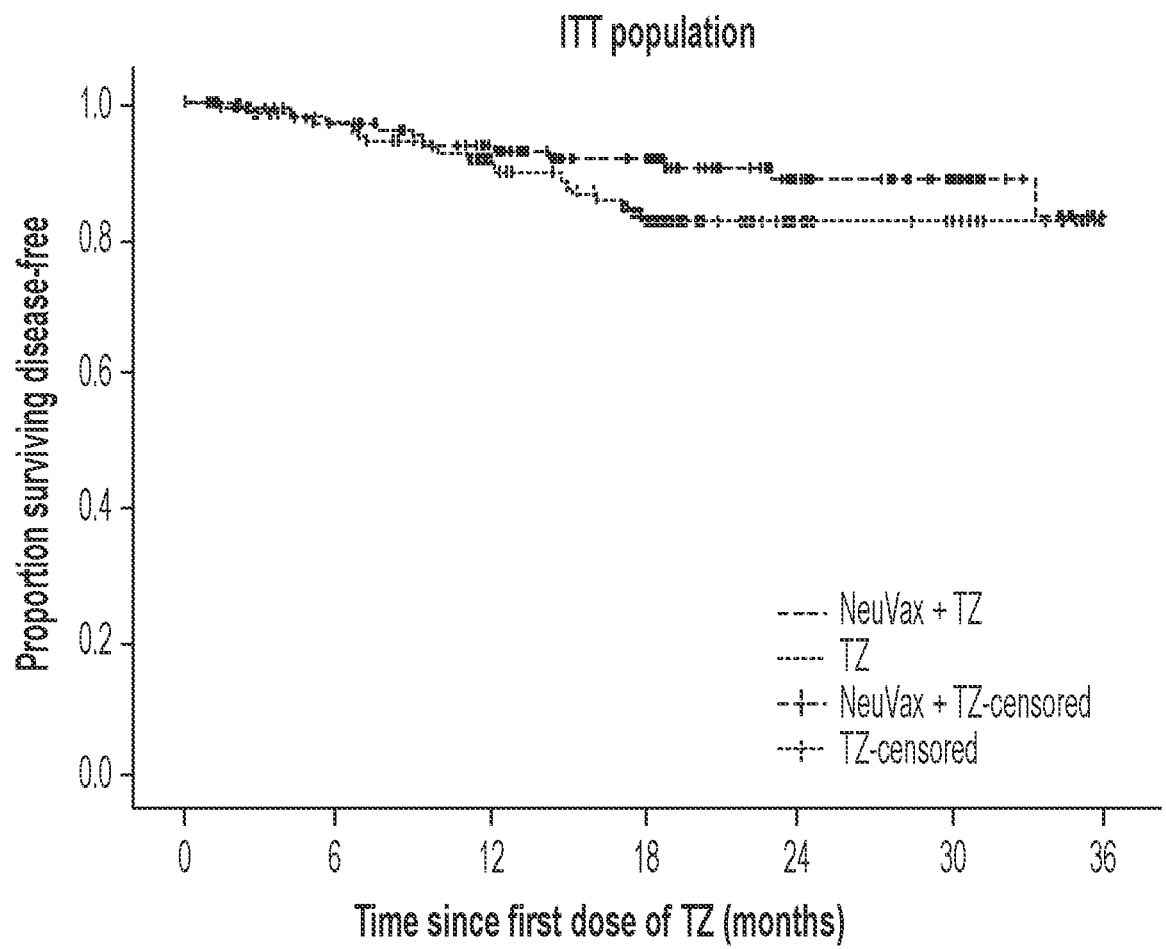
FIG. 5 shows a graph of disease-free survival, demonstrating a clinically meaningful difference in median DFS in favor of the combination arm (NeuVax+TZ) in the intention-to-treat (ITT) entire study population. NeuVax+TZ (N=136): 36-month DFS=83.1%; 24-month DFS=88.6%. TZ (N=139): 36-month DFS=82.5%; 24-month DFS=82.5%. Median follow up 19.6 (IQR 12.5-28.3) months; P value=0.257; Hazard ratio (HR)=0.67 (CI 0.33-1.35). Final analysis: Median follow up 25.7 months; P value=0.175; HR=0.62 (0.31-1.25). CI, confidence interval; DFS, disease-free survival; ITT, intent to treat; IQR, interquartile range; TZ, trastuzumab.
Figure 6:
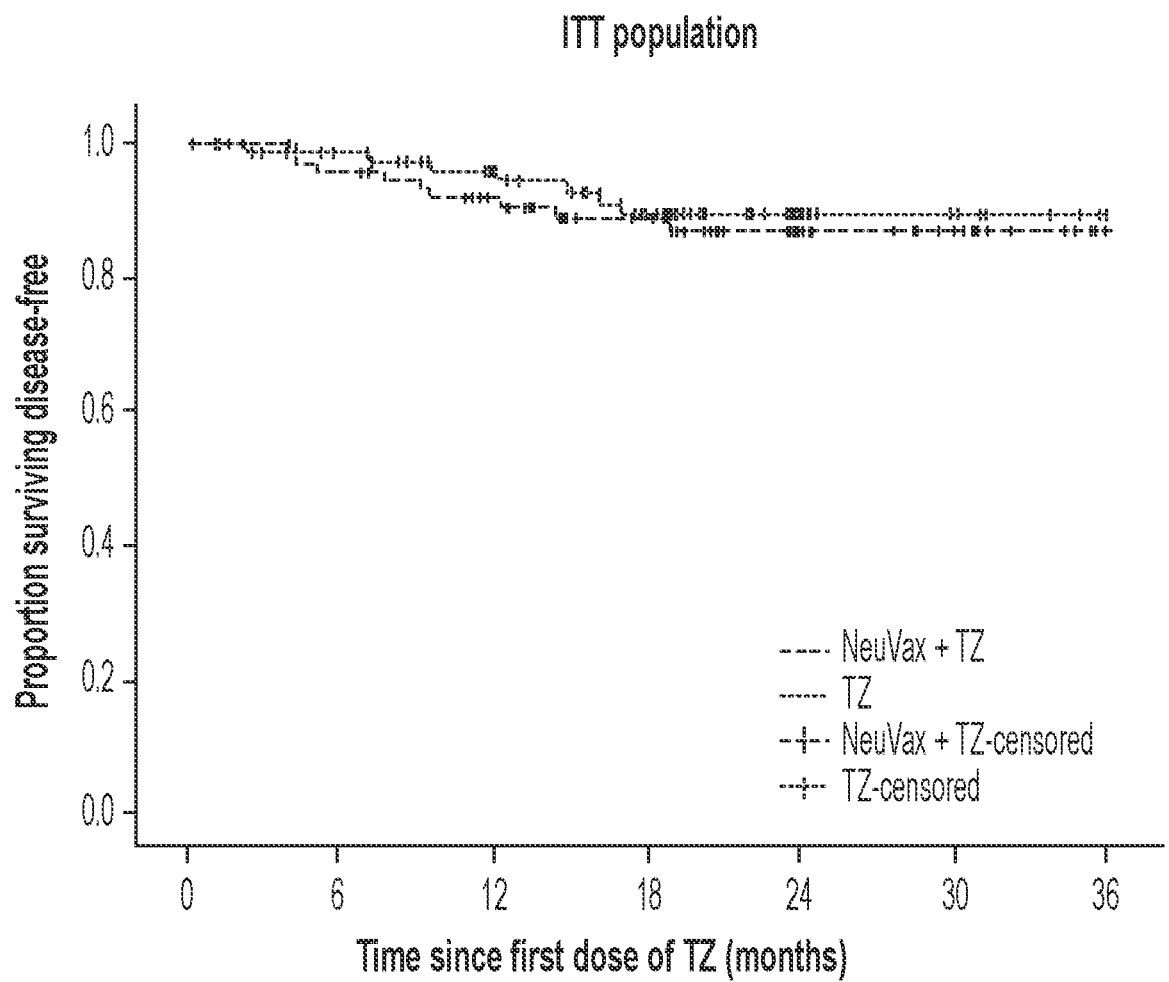
FIG. 6 shows a graph of disease-free survival in hormone receptor-positive (HR+) patients within the ITT population, demonstrating no difference in median DFS between groups. DFS was comparable to the NSAPB B-47 trial (89%), as well as several recent publications of early-stage TNBC trials where the natural history of the disease is followed up after standard front-line therapy. NeuVax+TZ (N=82): 36-month DFS=87.1%; 24-month DFS=87.1%. TZ (N=92): 36-month DFS=89.7%; 24-month DFS=89.7%. Median follow up 19.5 (IQR 15.4) months; P value=0.567; HR=0.55 (CI 0.27-1.10). Final analysis: Median follow up 25.4 months; P value—0.714; HR=1.19 (0.46-3.01). CI, confidence interval; DFS, disease-free survival; HR, hormone receptor; ITT, intent to treat; IQR, interquartile range; TZ, trastuzumab.

FIG. 3 shows a graph of maximum graded toxicity per patient. 7 patients in each arm did not start the assigned treatment and were excluded from safety analysis. There were no differences in the distribution or severity of related toxicities or maximum toxicities experienced by patients. There were no differences in individual local or systemic toxicities, except slightly more grade 1/2 localized pruritus and pain in the NeuVax group. TRAEs consisted primarily of manageable local injection site reactions, skin induration, pruritus and fatigue. There were no grade 4/5 TRAEs FIG. 4 is a graph of the cardiac ejection fraction (LVEF) over time. There were no significant differences in the rates of cardiac-related adverse events between the treatment arms (Table 2). The mean LVEF decreased from baseline slightly in both groups at the prespecified 3, 6, and 12-month evaluations ($p<0.02$) but did not differ after stopping trastuzumab at 24 months ($p>0.58$, FIG. 3). When evaluating all time points where the LVEF was evaluated with a linear mixed regression model, there were no significant differences in cardiac ejection fraction change over time ($p=0.65$), between randomization arm ($p=0.91$), or between the arms over time ($p=0.81$, FIG. 4).

TABLE 3

Recurrences

| Population | NeuVax + TZ Recurrence/Total (%) | TZ Recurrence/Total (%) | Log rank |
|---|---|---|---|
| ITT | 13/136 (9.6) | 19/139 (13.7) | 0.257 |
| ITT TNBC | 4/53 (7.5) | 12/45 (26.7) | 0.023 |

ITT, intent to treat; TNBC, triple negative breast cancer; TZ, trastuzumab.

Figure 7:
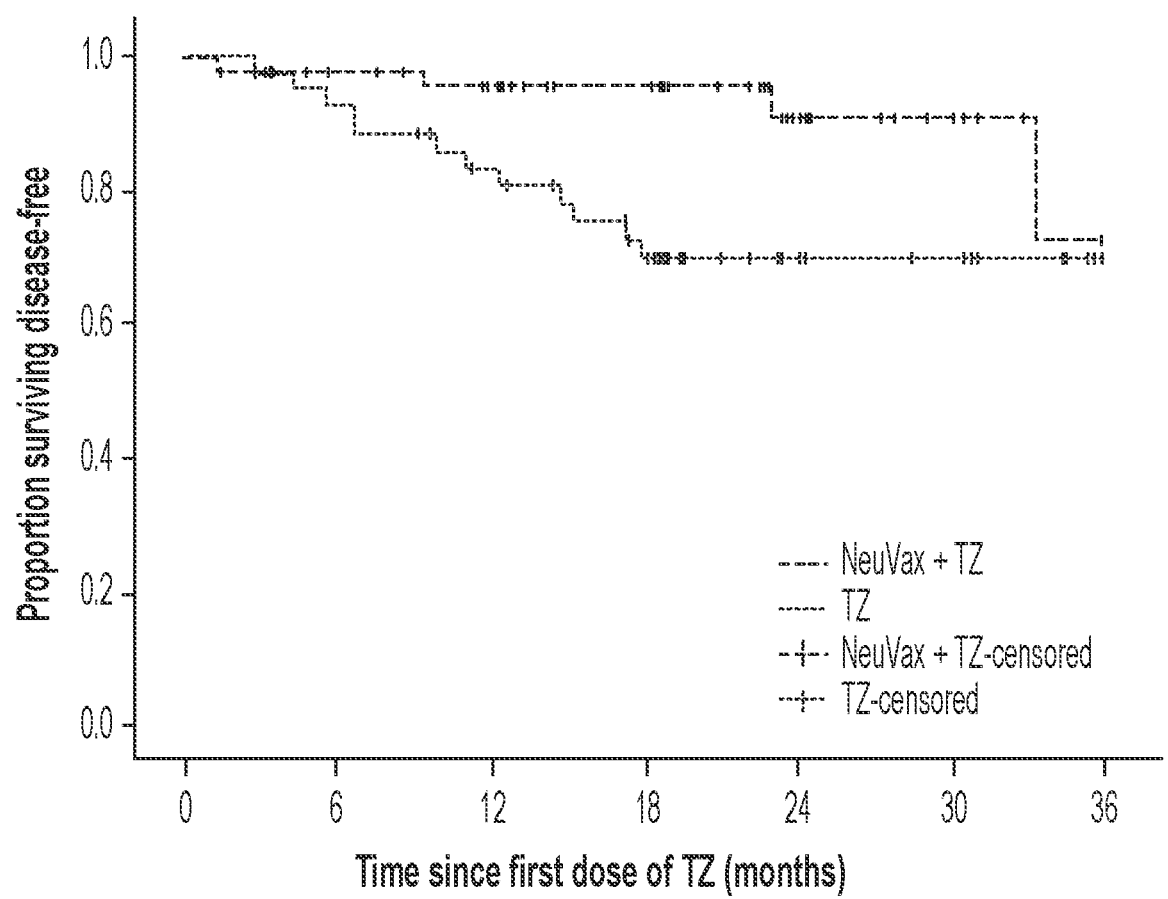
FIG. 7 shows a graph of disease-free survival in TNBC patients (defined as HR-negative, HER2 IHC 1+ or 2+), demonstrating clinically meaningful and statistically significant difference in median DFS in favor of the combination arm (NeuVax™+TZ). NeuVax+TZ (N=53): 36-month DFS=72.9%; 24-month DFS=91.1%. TZ (N=45): 36-month DFS=69.9%; 24-month DFS=69.9%. Median follow up 19.3 (IQR 12.8-28.0) months; P value=0.023; HR=0.26 (CI 0.09-0.90). Final analysis: Median follow up 26.1 months; P value=0.013; HR: 0.26 (0.08-0.81). DFS, disease-free survival; IQR, interquartile range; TNBC, triple negative breast cancer; TZ, trastuzumab.

FIG. 7 shows a graph of disease-free survival in TNBC patients. Within the pre-specified subgroup analysis, a much stronger clinical benefit was seen within the triple negative population.

This patient population warrants particular interest because, in an era of effective targeted therapies for breast cancer, these patients are left with very few effective therapies. As previously discussed, roughly 80% of breast cancer patients do not currently qualify for the effective HER2-targeted molecular therapies (such as trastuzumab and other HER2-binding macromolecules/antibodies), but roughly three quarters of these patients will have ER positive disease, which is relatively less aggressive and ensures they can receive hormonal therapies, which latter are also very effective. While these patients who harbor hormone receptor-positive, HER2 negative (including hormone receptor-positive, HER2 'low expressing') disease have a very good prognosis, about 20% of patients with triple negative disease are currently the most at risk biologic subset of breast cancer patients, with a particularly poor prognosis and relying solely on cytotoxic chemotherapy as the mainstay of their therapy. Importantly, this is true both in the metastatic and early-stage settings, as well as the adjuvant/maintenance setting after completion of successful primary front-line therapy for early-stage disease. Therefore, patients with TNBC represent an underserved population of breast cancer patients, in need of novel therapies.

The NeuVax+trastuzumab combination was found safe in this study, with no notable safety differences between treatment arms. There was no added cardiac toxicity. NeuVax+ trastuzumab may provide clinically meaningful benefit to patients with HER2 low-expressing breast cancers. Most importantly, the NeuVax+trastuzumab combination demonstrated a statistically significant improvement in DFS in patients with TNBC.

Figure 8:
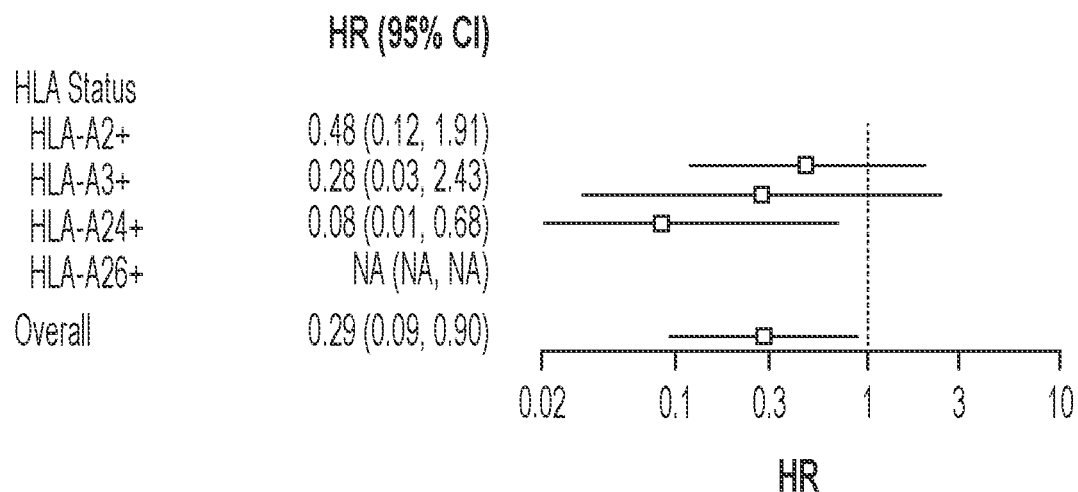
FIG. 8 shows a Forrest plot depicting relative benefit for all HLA-types among TNBC patients.

Example 2—Activity of NPS in HLA-A24+ Triple Negative (HER2 Low-Expressing) Breast Cancer Patients In patients in the triple negative breast cancer (TNBC) cohort (n=97) of this study (Example 1), active treatment (NPS plus trastuzumab) benefited all HLA-types (see FIG. 8, showing the forest plot for hazard ratios for the various HLA subtypes of patients within the trial, with a hazard ratio [H.R.] for the TNBC cohort at large—across HLA types—being a very impressive 0.29). However, this forest plot subgroup analysis showed the lowest H.R. achieved in patients who were HLA-A24+, with a remarkable H.R. value of 0.08 and a p-value of 0.003. HLA-A24 positivity is particularly pertinent to Asian/Pacific Basin populations.

Figure 9:
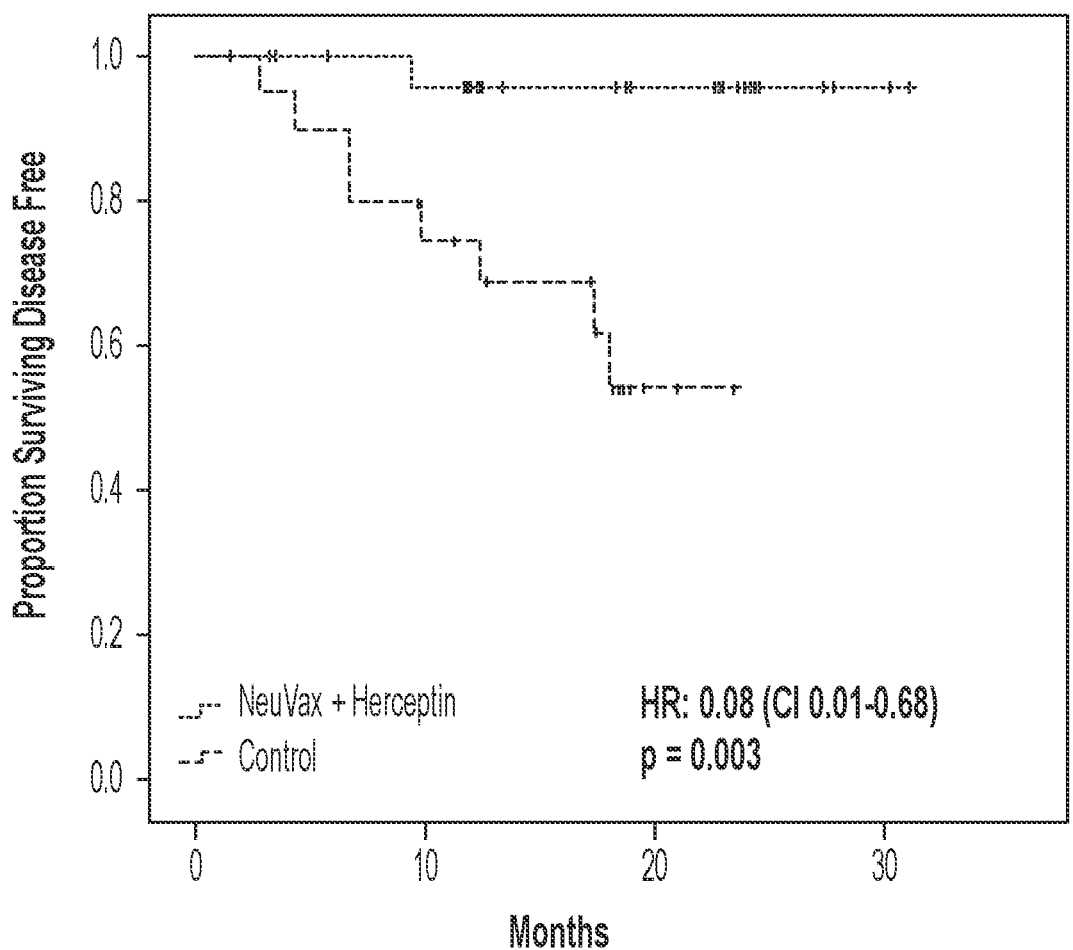
FIG. 9 shows Kaplan-Meier estimated DFS for HLA-A24+ TNBC patients.

In FIG. 9, DFS for HLA-A24+ TNBC patients is shown. In the latter subgroup of patients with TNBC, the NPS plus trastuzumab combination is associated with a notable 90.6% decrease in the relative risk of relapse or death at 24 months versus the control (trastuzumab only) arm in the 24-month DFS landmark analysis.

The data in FIGS. 8 and 9 confirm that the HLA-A24+ subgroup of TNBC patients demonstrates the highest clinical activity ever observed—as assessed by delta (DFS) between active (combo NPS+Trastuzumab) and control (trastuzumab alone)—among all other subgroups of patients tested (such subgroups being defined according to various baseline patient and disease features and data stratification parameters).

Figure 10:
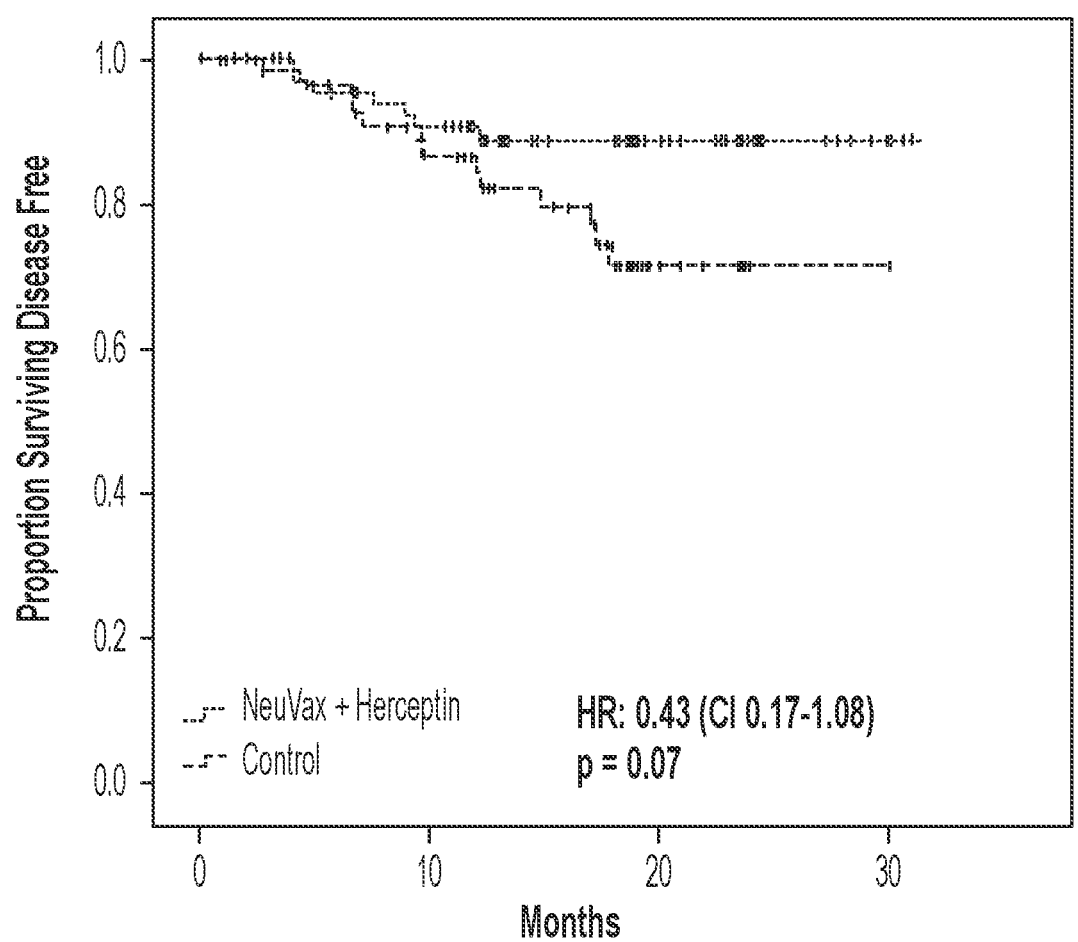
FIG. 10 shows Kaplan Meier estimated DFS for all HLA-A24+ patients.

Additionally, HLA-A24+ patients also showed a trend toward improved DFS study-wide (i.e., in the HLA-A24+ portion of the ITT population, which includes both TNBC and non-TNBC patients) (see FIG. 10). In this analysis for median DFS for HLA-A24+ patients within the ITT (study population at large) showed an H.R. of 0.43 with a value of 0.07, corresponding to 61.2% decrease in the relative risk of relapse or death at 24 months with the combination (NPS+ trastuzumab) versus the control (trastuzumab only) arm in the 24-month DFS landmark analysis.

Thus, the strongest clinical effect ever seen with the NPS plus trastuzumab combination was in HLA-A24+ patients, both for the TNBC cohort and the ITT population (the latter being HER2 IHC 1+/2+ irrespective of hormone receptor status). This observation is very intriguing for at least two reasons.

First, HLA-A24 is the most heavily expressed HLA type in populations living in the Asian/Pacific basin region and this renders the finding very pertinent to the Asian markets, in that these data strongly position NPS biologically as an agent that could potentially be used (in combination with trastuzumab) optimally in these territories, while still active across the globe, considering the very high prevalence of the HLA-A24 allele in Asia.

Second, this finding could not have been predicted when one looks at the binding affinities of the various HLA subtypes to the E75 (NPS) peptide. In fact, HLA-A24 (and A26) molecules (highly prevalently expressed in Asian patients) have the lowest binding activity for the NPS peptide (see Table 4), but yet are associated with the most potent clinical response (per DFS clinical outcome data above).

In Table 4, below, artificial neural networks (ANN) IC50 denote the concentration of protein required for 50% binding with MHC Class I. Low IC50 values denote strong binding the antigen-recognizing biophysical 'pocket' of a given HLA molecule, and conversely high IC50 values denote weak binding to the said 'pocket'.

TABLE 4

Predicted binding affinity for E75 (NPS) HER2 epitope among test HLA types.

| Allele | Peptide | Rank | ANN IC50 |
|---|---|---|---|
| HLA-A 02:06 | KIFGSLAFL | 0.62 | 10.84 |
| HLA-A 02:01 | KIFGSLAFL | 1.2 | 14.35 |
| HLA-A 03:01 | KIFGSLAFL | 3.65 | 2110.2 |
| HLA-A 26:01 | KIFGSLAFL | 8.6 | 13395.81 |
| HLA-A 24:02 | KIFGSLAFL | 13.15 | 9730.14 |

TABLE 5

Demographics of HLA-A24+ patients

| | Vaccine Group n = 71 (53.4%) | Control Group n = 62 (46.6%) | p value |
|---|---|---|---|
| Race | | | |
| White | 51 (71.8%) | 43 (69.4%) | 0.59 |
| Asian | 2 (2.8%) | 0 (0.0%) | |
| Black | 10 (14.1%) | 12 (19.4%) | |
| Hispanic | 6 (8.5%) | 6 (8.1%) | |
| Other/Unknown | 2 (2.8%) | 2 (3.2%) | |
| Stage | | | |
| <III | 37 (52.1%) | 29 (46.8%) | 0.71 |
| >=III | 34 (47.9%) | 33 (53.2%) | |
| Breast Procedure | | | |
| Lumpectomy | 19 (26.8%) | 18 (29.0%) | 0.61 |
| Mastectomy | 51 (71.8%) | 41 (66.1%) | |
| Lumpectomy followed by Mastectomy | 1 (1.4%) | 2 (3.2%) | |
| None | 0 (0.0%) | 1 (1.6%) | |
| Age (Median) | 53 | 51 | 0.93 |
| Axillary Procedure | | | |
| Sentinel Lymph Node Biopsy | 26 (36.6%) | 19 (30.7%) | 0.48 |
| Axillary Dissection | 36 (50.7%) | 30 (48.4%) | |
| SLN Biopsy followed by Axillary Dissection | 9 (12.7%) | 12 (19.4%) | |
| None | 0 (0.0%) | 1 (1.6%) | |
| Chemotherapy | | | |
| Neoadjuvant | 39 (54.9%) | 35 (56.5%) | 0.97 |
| Adjuvant | 29 (40.9%) | 24 (38.7%) | |
| None | 4 (5.6%) | 3 (4.8%) | |
| Radiation Therapy | | | |
| Neoadjuvant | 2 (2.8%) | 0 (0.0%) | 0.02* |
| Adjuvant | 54 (76.1%) | 58 (93.6%) | |
| None | 15 (21.1%) | 4 (6.5%) | |

As is evident from Table 4, the highest IC50 values for peptide binding are yielded for alleles HLA-A24 (and A-26). When assessed by rank of strength of binding by modeling (which includes additional factors on top of the IC50) it is the HLA-A24 subtype that demonstrates the weakest association with the NPS peptide among all four major HLA Class I alleles (A02, A03, A24 [and in this case even A26]).

The above, taken together, suggest that NPS is able to bind to both the lower-affinity MHC-I conformations (A24) in addition to the high-affinity conformations, i.e., A02 and A03, especially in Asian populations. In fact, this ability of associating at a biophysical/molecular level with both these HLA conformations could be—at least in part—responsible for the generation of an optimally favorable immunologic response against the antigen we are vaccinating with (NPS), and most likely other HER2 fragments at large. It is predicted that this is most likely the case across several additional HER2 epitopes, epitope spreading post-NPS vaccination has been shown repeatedly in earlier studies (Conrad H et al. *J Immunol.* 2008; 180:8135-45; Emens L A et al. *Endocr Relat Cancer.* 2005; 12:1-17; Mittendorf E A et al., *Surgery.* 2006; 139:407-18; Disis M L et al., *J Clin Oncol.* 2002; 20:2624-32; Brossart P et al. *Blood.* 2000; 96:3102-8; Disis M L et al., *Clin Cancer Res.* 1999; 5:1289-97).

The fact that a deep clinical response is seen in HLA-A24+ patients post-NPS vaccination in the face of low affinity of NPS for the actual HLA-A24 molecule (an apparent paradox) is most likely due to decreased "exposure" of the host's antigen presenting cells (antigen-presenting cells (APCs), i.e., macrophages and monocytes)—and eventually CD8 T-cells- to the NPS epitope in HLA-A24 individuals (due to lower frequency of antigen recognition 'events' by the immune system). Thus, the effect is likely due to a decreased rate of emergence of tolerance to this critical epitope (NPS). In other words, lower affinity of peptide binding may be the basis for inefficient tolerization to many HLA-A24-binding self-peptides (including NPS) in Asian populations. This is important, as peptide vaccines other than NPS (especially monovalent ones) with higher affinity to HLA-A24 can be rapidly tolerogenic (despite induction of 'decent' levels of early immune reactivity) and lead to progressively diminishing immunogenicity over time; moreover, this effect may be more enhanced in HLA-A24+ individuals. This is then an effect we do not expect to see with NPS, especially in Asian populations, which is a very positive and strikingly differentiating attribute of NPS.

All of the above can provide potentially strong differentiation of NPS (or NPS variants) versus other HER2-targeting immunotherapeutics (including peptidic or other types of vaccines), especially in Asian patients, as such agents could demonstrate either too low of an affinity with HLA-A24, in which case they would be more poorly antigenic/immunogenic versus. NPS, or too high of an affinity with HLA-A24, in which case they would lead more rapidly and definitively toward immune tolerance and anergy toward a given antigen. It also known in the general peptide vaccine literature that a higher threshold of peptide-HLA avidity may be required to induce immune tolerance as compared to the threshold of peptide-HLA avidity required to immunize T cells. Thus, in most cases of peptide vaccine antigens, the balance tips strongly in one of 2 directions: immunogenicity vs. tolerance induction. In sum, the above findings show that serendipitously, and quite advantageously, it seems that NPS is both optimally antigenic and anti-tolerogenic (specifically in the context of patients with HLA-A24), and this may well be a feature that is unique and 'peculiar' to NPS (and NPS variants).

Finally, there is fundamental/general (i.e., not specific or pertinent to NPS) literature (see list shown with an asterisk [*] below) positively correlating the weakness of the association of a given self-antigen (i.e., intrinsically 'weak' antigen, as most tumor-associated antigens are, including NPS) to its cognate HLA/MHC Class I 'pocket' and lack of tolerogenicity toward that said antigen (the latter property being an optimal property for anticancer vaccines, which NPS seems to possess). Finally, it is of great interest that this anti-tolerogenic property of NPS may underlie the activation and persistence of NPS-specific CD4 (i.e., T-memory) cell clones in vaccinated patients, which is a rare (also very beneficial from a clinical perspective) property of NPS (see: Peoples GE et al. *Clin Cancer Res.* 2008; 14:797-803; which is the key paper demonstrating good CD4 T-memory cell responses post-NPS vaccination, which would be unexpected with a mainly CD8-activating short [9-aminoacid] peptide like NPS).

*Citations re. relationship between HLA avidity of antigens and tolerogenicity (in cancer immunotherapy, but not directly pertinent to NPS) are listed below:

Blum J S et al. Annu Rev Immunol. 2013; 31:443-73.
Janicki C N et al. Cancer Res. 2008; 68:2993-3000.
Gebreselassie D et al. Hum Immunol. 2006; 67:894-906.
Gross D A et al. J Clin Invest. 2004; 113:425-33.
McMahan C and Fink P. J Immunol. 2000; 165:6902-7.
Arnold B et al. Immunol Today. 1993; 14:12-4.
Nikolić-Zugić J & Carbone F R. Immunol Res. 1991; 10:54-65.
Milich D R et al. J Immunol. 1989; 143:3148-56.

EXEMPLIFIED EMBODIMENTS

Examples of embodiments of the invention include, but are not limited to: Embodiment 1. A method for treating triple-negative breast cancer (TNBC) in an individual, comprising administering to the individual: (a) an effective amount of trastuzumab or derivative thereof; and (b) an effective amount of nelipepimut-S, or variant thereof.

Embodiment 2. The method of embodiment 1, wherein the trastuzumab, or derivative thereof, and the nelipepimut-S, or variant thereof, are administered at intervals, and administration of the nelipepimut-S, or variant thereof, is initiated after initiation of administration of the trastuzumab or derivative thereof.

Embodiment 3. The method of embodiment 1 or 2, wherein the method comprises initiation of a preparatory phase comprising periodic administration of doses of trastuzumab or derivative, without nelipepimut-S or variant, followed by a combination phase comprising periodic administration of doses of both the trastuzumab or derivative, and nelipepimut-S or variant.

Embodiment 4. The method of embodiment 3, wherein the preparatory phase comprises a frequency and duration of administration of trastuzumab or derivative thereof sufficient to increase the major histocompatibility complex type I-mediated presentation of HER2 antigen on breast cancer cells of the individual following said administering of the nelipepimut-S or variant thereof.

Embodiment 5. The method of any preceding embodiment, wherein administration of the nelipepimut-S or variant during the initial immunization phase is initiated after completion of the third, fourth, or fifth administration of trastuzumab or derivative thereof.

Embodiment 6. The method of any preceding embodiment, wherein the trastuzumab or derivative thereof is administered at an initial loading dose of 8 mg/kg and maintenance doses of 6 mg/kg every three weeks (q3wk), and wherein a dose of 1,000 mcg of the nelipepimut-S or variant is administered.

Embodiment 7. The method of any preceding embodiment, wherein the TNBC has a HER2 expression of 1+ or 2+ by immunohistochemistry (IHC).

Embodiment 8. The method of any preceding embodiment, wherein the individual is HLA-A2 positive, HLA-A3 positive, HLA-A24 positive, or HLA-A26 positive.

Embodiment 9. The method of any preceding embodiment, wherein the individual is clinically disease-free at the time of said administering, after receiving standard of care therapy for the TNBC (e.g., chemotherapy, surgical primary tumor extirpation, radiation therapy, or a combination of two or more of the foregoing).

Embodiment 10. The method of embodiment 9, wherein administration of trastuzumab or derivative thereof is initiated between three weeks and twelve weeks after completion of the standard of care therapy.

Embodiment 11. The method of any preceding embodiment, wherein the TNBC is node-negative (e.g., AJCC N0 or N0(i+)) at the time of said administering.

Embodiment 12. The method of any preceding embodiment, wherein the trastuzumab or derivative thereof is administered intravenously.

Embodiment 13. The method of any preceding embodiment, wherein the nelipepimut-S, or variant thereof, is administered intradermally.

Embodiment 14. The method of any preceding embodiment, further comprising administering an immunologic adjuvant to the individual.

Embodiment 15. The method of embodiment 12, wherein the immunologic adjuvant comprises granulocyte-macrophage colony stimulating factor (GM-CSF).

Embodiment 16. The method of embodiment 15, wherein a dose of 250 mcg of GM-CSF is administered per day.

Embodiment 17. The method of any one of embodiments 14-16, wherein the immunologic adjuvant is administered every three weeks (q3wk).

Embodiment 18. The method of any preceding embodiment, wherein 1,000 mcg of the nelipepimut-S or variant thereof and 250 mcg of the GM-CSF are administered intradermally every three weeks, 30-120 minutes after completion of infusion of trastuzumab or derivative thereof.

Embodiment 19. The method of any one of embodiments 14 to 18, wherein the immunologic adjuvant is administered with the nelipepimut-S, or variant thereof, within the same or separate formulations.

Embodiment 20. The method of any preceding embodiment, wherein the nelipepimut-S comprises a HER2/neu peptide consisting of the amino acid sequence KIFGSLAFL (SEQ ID NO:1), and the variant has an alpha-aminobutyric acid, norvaline or norleucine at position 4 of SEQ ID NO:1, an alpha.-aminobutyric acid, norvaline or norleucine at position 7 of SEQ ID NO:1, or an isophenylalanine at position 8 of SEQ ID NO:1.

Embodiment 21. The method of embodiment 20, wherein the variant of nelipepimut-S is administered, and the variant is selected from among:

```
                        (SEQ ID NO: 2)
        K I F Abu S L A F L;

(SEQ ID NO: 3)
        K I F Nva S L A F L;

(SEQ ID NO: 4)
        K I F Nle S L A F L;

(SEQ ID NO: 5)
        K I F G S L Abu F L;

(SEQ ID NO: 6)
        K I F G S L Nva F L;

(SEQ ID NO: 7)
        K I F G S L Nle F L;
```

-continued and

K I F G S L A isoF L.　(SEQ ID NO: 8)

Embodiment 22. The method of any preceding embodiment, wherein the method further comprises administering an additional therapeutic agent to the subject before, during, or after administration of the trastuzumab, or derivative thereof, and nelipepimut-S, or variant thereof.

Embodiment 23. The method of embodiment 22, wherein the additional therapeutic agent is an immunotherapeutic agent.

Embodiment 24. The method of embodiment 23, wherein the immunotherapeutic agent comprises an immune checkpoint inhibitor.

Embodiment 25. The method of any preceding embodiment, wherein said administering reduces tumor size and/or increases the individual's disease-free survival (relapse-free survival).

Embodiment 26. The method of any preceding embodiment, wherein administration of trastuzumab, or derivative thereof, and the nelipepimut-S, or variant thereof, has a synergistic effect on the individual.

Embodiment 27. The method of any preceding embodiment, wherein the method further comprises administering an additional therapeutic agent to the individual before, during, or after administration of the trastuzumab, or derivative thereof, and nelipepimut-S, or variant thereof.

Embodiment 28. The method of embodiment 27, wherein the additional therapeutic agent is an immunotherapeutic agent.

Embodiment 29. The method of embodiment 28, wherein the immunotherapeutic agent comprises an immune checkpoint inhibitor.

Embodiment 30. The method of any preceding embodiment, wherein the individual is clinically disease-free at the time of said administering, after receiving therapy for the TNBC (e.g., chemotherapy, surgical primary tumor extirpation, radiation therapy, or a combination of two or more of the foregoing), and wherein the method delays or prevents recurrence of the TNBC in the individual.

Embodiment 31. The method of any preceding embodiment, wherein administration of trastuzumab, or derivative thereof, and the nelipepimut-S, or variant thereof, have a synergistic effect on the individual.

Embodiment 32. The method of any preceding embodiment, wherein an effective amount of trastuzumab and an effective amount of nelipepimut-S are administered to the individual.

Embodiment 33. A method of inducing an immune response to HER2/neu in an individual with a triple-negative breast cancer expressing low levels of HER2/neu, the method comprising administering to the individual: (a) an effective amount of trastuzumab, or derivative thereof; and (b) an effective amount of nelipepimut-S, or variant thereof.

Embodiment 34. The method of embodiment 33, wherein the trastuzumab, or derivative thereof, and the nelipepimut-S, or variant thereof, are administered at intervals, and administration of the nelipepimut-S, or variant thereof, is initiated after initiation of administration of the trastuzumab or derivative thereof.

Embodiment 35. The method of embodiment 33 or 34, wherein the method comprises initiation of a preparatory phase comprising periodic administration of doses of trastuzumab or derivative thereof without nelipepimut-S or variant, followed by a combination phase comprising periodic administration of doses of both the trastuzumab or derivative thereof, and nelipepimut-S or variant thereof.

Embodiment 36. The method of embodiment 35, wherein the preparatory phase comprises a frequency and duration of administration of trastuzumab or derivative thereof sufficient to increase the major histocompatibility complex type I-mediated presentation of HER2 antigen on breast cancer cells of the individual following said administering of the nelipepimut-S or variant thereof.

Embodiment 37. The method of any preceding embodiment, wherein administration of the nelipepimut-S or variant is initiated after completion of the third, fourth, or fifth administration of trastuzumab or derivative thereof.

Embodiment 38. The method of any preceding embodiment, wherein the trastuzumab or derivative thereof is administered at an initial loading dose of 8 mg/kg and maintenance doses of 6 mg/kg every three weeks (q3wk), and wherein a dose of 1,000 mcg of the nelipepimut-S or variant is administered.

Embodiment 39. The method of any preceding embodiment, wherein the TNBC has a HER2 expression of 1+ or 2+ by immunohistochemistry (IHC).

Embodiment 40. The method of any preceding embodiment, wherein the individual is HLA-A2 positive, HLA-A3 positive, HLA-A24 positive, or HLA-A26 positive.

Embodiment 41. The method of any preceding embodiment, wherein the individual is HLA-A24 positive.

Embodiment 42. The method of any preceding embodiment, wherein the individual is clinically disease-free at the time of said administering, after receiving standard of care therapy for the TNBC (e.g., surgical primary tumor extirpation, chemotherapy, radiation therapy, or a combination of two or more of the foregoing).

Embodiment 43. The method of embodiment 42, wherein administration of trastuzumab or derivative thereof is initiated between three weeks and twelve weeks after completion of the standard of care therapy.

Embodiment 44. The method of any preceding embodiment, wherein the TNBC is node-negative (e.g., AJCC N0 or N0(i+)) at the time of said administering.

Embodiment 45. The method of any preceding embodiment, wherein the trastuzumab or derivative thereof is administered intravenously.

Embodiment 46. The method of any preceding embodiment, wherein the nelipepimut-S, or variant thereof, is administered intradermally.

Embodiment 47. The method of any preceding embodiment, further comprising administering an immunologic adjuvant.

Embodiment 48. The method of embodiment 47, wherein the immunologic adjuvant is administered with the nelipepimut-S, or variant thereof, within the same or separate formulations.

Embodiment 49. The method of embodiment 47 or 48, wherein the immunologic adjuvant is administered intradermally.

Embodiment 50. The method of any one of embodiments 47 to 49, wherein the immunologic adjuvant comprises granulocyte-macrophage colony stimulating factor (GM-CSF).

Embodiment 51. The method of embodiment 49, wherein a dose of 250 mcg of GM-CSF is administered per day.

Embodiment 52. The method of any one of embodiments 46-50, wherein the immunologic adjuvant is administered every three weeks (q3wk).

Embodiment 53. The method of any preceding embodiment, wherein 1,000 mcg of the nelipepimut-S or variant thereof, and 250 mcg of the GM-CSF, are administered intradermally every three weeks, 30-120 minutes after completion of trastuzumab or derivative infusion.

Embodiment 54. The method of any preceding embodiment, wherein the nelipepimut-S comprises a HER2/neu peptide consisting of the amino acid sequence KIFGSLAFL (SEQ ID NO:1), and the variant has an alpha-aminobutyric acid, norvaline or norleucine at position 4 of SEQ ID NO:1, an alpha-aminobutyric acid, norvaline or norleucine at position 7 of SEQ ID NO:1, or an isophenylalanine at position 8 of SEQ ID NO:1.

Embodiment 55. The method of embodiment 54, wherein the variant of nelipepimut-S is administered, and the variant is selected from among:

| | (SEQ ID NO: 2) |
|---|---|
| K I F Abu S L A F L; | |

| | (SEQ ID NO: 3) |
|---|---|
| K I F Nva S L A F L; | |

| | (SEQ ID NO: 4) |
|---|---|
| K I F Nle S L A F L; | |

| | (SEQ ID NO: 5) |
|---|---|
| K I F G S L Abu F L; | |

| | (SEQ ID NO: 6) |
|---|---|
| K I F G S L Nva F L; | |

| | (SEQ ID NO: 7) |
|---|---|
| K I F G S L Nle F L; and | |

| | (SEQ ID NO: 8) |
|---|---|
| K I F G S L A isoF L. | |

Embodiment 56. The method of any preceding embodiment, wherein the administration of the nelipepimut-S or variant thereof represents a primary vaccination, and wherein the method further comprises, after completion of the primary vaccination, administering 1, 2, 3, 4, or more booster doses of nelipepimut-S or variant thereof, up to 30 months or longer, optionally with an immunologic adjuvant (e.g., GM-CSF), at a lesser frequency than the primary vaccination.

Embodiment 57. The method of embodiment 56, wherein two or more booster doses of nelipepimut-S or variant thereof are administered, and wherein one booster dose is administered every 6 months.

Embodiment 58. The method of any preceding embodiment, wherein the method further comprises administering an additional therapeutic agent to the individual before, during, or after administration of the trastuzumab, or derivative thereof, and nelipepimut-S, or variant thereof.

Embodiment 59. The method of embodiment 58, wherein the additional therapeutic agent is an immunotherapeutic agent.

Embodiment 60. The method of embodiment 59, wherein the immunotherapeutic agent comprises an immune checkpoint inhibitor.

Embodiment 61. The method of any preceding embodiment, wherein said administering reduces tumor size and/or increases the individual's disease-free survival (relapse-free survival).

Embodiment 62. The method of any preceding embodiment, wherein the individual is clinically disease-free at the time of said administering, after receiving therapy for the TNBC (e.g., chemotherapy, surgical primary tumor extirpation, radiation therapy, or a combination of two or more of the foregoing), and wherein the method delays or prevents recurrence of the TNBC in the individual.

Embodiment 63. The method of any preceding embodiment, wherein administration of trastuzumab, or derivative thereof, and the nelipepimut-S, or variant thereof, have a synergistic effect on the individual.

Embodiment 64. The method of any preceding embodiment, wherein an effective amount of trastuzumab and an effective amount of nelipepimut-S are administered to the individual.

Embodiment 65. A medicament comprising nelipepimut-S, or variant thereof, for use in combination with trastuzumab, or derivative thereof, for treating triple-negative breast cancer in an individual.

Embodiment 66. The medicament of embodiment 65, further comprising an immunologic adjuvant.

Embodiment 67. The medicament of embodiment 65, wherein the immunologic adjuvant comprises granulocyte-macrophage colony stimulating factor (GM-CSF).

Embodiment 68. A medicament comprising trastuzumab, or derivative thereof, for use in combination with nelipepimut-S, or variant thereof, for treating triple-negative breast cancer (TNBC) in an individual.

Embodiment 69. A kit which comprises a first container, a second container and a package insert, wherein the first container comprises at least one dose of a medicament comprising trastuzumab, or derivative thereof, the second container comprises at least one dose of a medicament comprising nelipepimut-S, or variant thereof, and the package insert comprises instructions for treating an individual for triple-negative breast cancer using the medicaments.

Embodiment 70. The kit of embodiment 69, further comprising an immunologic adjuvant, wherein the immunologic adjuvant is in a third container or is in the second container with the nelipepimut-S, or variant thereof.

Embodiment 71. The kit of embodiment 69 or 70, wherein the immunologic adjuvant comprises granulocyte-macrophage colony stimulating factor (GM-CSF).

Embodiment 72. The kit of embodiment 69 or 70, wherein the kit comprises trastuzumab and nelipepimut-S.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Fehrenbacher, L. et al. *SABCS*, 2017; Abstract GS1-02.
Mittendorf, E. et al. *Ann Oncol.*, 2014, 25:1735-1742.
Gall, V. et al. *Cancer Res.*, 2017, 77:5374-5383.

We claim:

1. A method for increasing disease-free survival in an individual who has, or has had, triple-negative breast cancer (TNBC), comprising administering to the individual: (a) an effective amount of trastuzumab; and (b) an effective amount of nelipepimut-S, wherein the TNBC is hormone receptor-negative, and has HER2/neu expression of 1+ or 2+ by immunohistochemistry (IHC) and is negative for amplification of the HER2/neu gene by fluorescent in situ hybridization (FISH), and wherein the method comprises initiation of a preparatory phase comprising periodic administration of doses of the trastuzumab without the nelipepimut-S, followed by a combination phase comprising periodic administration of doses of both the trastuzumab and the nelipepimut-S, wherein the method results in increased disease-free survival compared to individuals administered trastuzumab without nelipepimut-S.

2. The method of claim 1, wherein the preparatory phase comprises a frequency and duration of administration of trastuzumab, sufficient to increase the major histocompatibility complex type I-mediated presentation of HER2 antigen on breast cancer cells of the individual following said administering of the nelipepimut-S.

3. The method of claim 1, wherein administration of the nelipepimut-S is initiated after completion of the third, fourth, or fifth administration of trastuzumab.

4. The method of claim 1, wherein the trastuzumab is administered at an initial loading dose of 8 mg/kg and maintenance doses of 6 mg/kg every three weeks (q3wk), and wherein a dose of 1,000 mcg of the nelipepimut-S is administered.

5. The method of claim 1, wherein the individual has an HLA type that is any of HLA-A2 positive, HLA-A3 positive, HLA-A24 positive, or HLA-A26 positive.

6. The method of claim 1, wherein the individual is clinically disease-free at the time of said administering, after receiving standard of care therapy for the TNBC.

7. The method of claim 6, wherein administration of trastuzumab is initiated between three weeks and twelve weeks after completion of the standard of care therapy.

8. The method of claim 1, wherein the trastuzumab is administered intravenously, and the nelipepimut-S is administered intradermally.

9. The method of claim 1, further comprising administering an immunologic adjuvant to the individual.

10. The method of claim 9, wherein the immunologic adjuvant comprises granulocyte-macrophage colony stimulating factor (GM-CSF).

11. The method of claim 10, wherein 1,000 mcg of the nelipepimut-S and 250 mcg of the GM-CSF are administered intradermally every three weeks, 30-120 minutes after completion of trastuzumab infusion.

12. The method of claim 1, wherein the individual is clinically disease-free at the time of said administering, after receiving therapy for the TNBC, and wherein the method delays or prevents recurrence of the TNBC in the individual.

13. A method of inducing an immune response to HER2/neu in an individual who has, or has had, triple-negative breast cancer (TNBC) expressing low levels of HER2/neu, the method comprising administering to the individual: (a) an effective amount of trastuzumab; and (b) an effective amount of nelipepimut-S, wherein the TNBC is hormone receptor-negative, and has HER2 expression of 1+ or 2+ by immunohistochemistry (IHC) and is fluorescent in situ hybridization (FISH) non-amplified, and wherein the method comprises initiation of a preparatory phase comprising periodic administration of doses of the trastuzumab without the nelipepimut-S, followed by a combination phase comprising periodic administration of doses of both the trastuzumab and the nelipepimut-S, wherein the method results in increased disease-free survival compared to individuals administered trastuzumab without nelipepimut-S.

14. The method of claim 1, further comprising administering one or more booster doses of nelipepimut-S to the individual following the combination phase.

15. The method of claim 14, wherein two or more booster doses are administered, and wherein one booster dose is administered every 6 months.

16. The method of claim 13, further comprising administering one or more booster doses of the nelipepimut-S to the individual following the combination phase.

17. The method of claim 16, wherein two or more booster doses are administered, and wherein one booster dose is administered every 6 months.

18. The method of claim 1, wherein the method further comprises administering a checkpoint inhibitor to the subject before, during, or after administration of the trastuzumab and nelipepimut-S.

19. The method of claim 13, wherein the method further comprises administering a checkpoint inhibitor to the subject before, during, or after administration of the trastuzumab and nelipepimut-S.

20. The method of claim 13, wherein the individual has an HLA type that is any of HLA-A2 positive, HLA-A3 positive, HLA-A24 positive, or HLA-A26 positive.

21. The method of claim 13, wherein the individual is HLA-A24 positive.

22. A method for increasing disease-free survival in an HLA-A24 positive individual who has, or has had, triple-negative breast cancer (TNBC), comprising administering to the HLA-24 positive individual: (a) an effective amount of trastuzumab; and (b) an effective amount of nelipepimut-S, wherein the TNBC is hormone receptor-negative, and has HER2/neu expression of 1+ or 2+ by immunohistochemistry (IHC) and is negative for amplification of the HER2/neu gene by fluorescent in situ hybridization (FISH), wherein the method comprises initiation of a preparatory phase comprising periodic administration of doses of the trastuzumab without the nelipepimut-S, followed by a combination phase comprising periodic administration of doses of both the trastuzumab and the nelipepimut-S, and wherein the method results in increased disease-free survival compared to individuals administered trastuzumab without nelipepimut-S.

* * * * *

UNITED STATES PATENT AND TRADEMARK OFFICE
CERTIFICATE OF CORRECTION

PATENT NO. : 11,564,987 B2
APPLICATION NO. : 16/658047
DATED : January 31, 2023
INVENTOR(S) : George E. Peoples et al.

It is certified that error appears in the above-identified patent and that said Letters Patent is hereby corrected as shown below:

In the Specification

Column 5,
Line 60, "position 7: K I F G S L Ne F L" should read --position 7: K I F G S L Nle F L--

Column 21,
Line 31, "every three weeks×6" should read --every three weeks × 6--
Line 32, "every six months×4" should read --every six months × 4--

Column 29,
Lines 12-18, "KIFGSLAFL" should read --KIFGSLAFL (SEQ ID NO: 1)--

Signed and Sealed this
Twenty-eighth Day of May, 2024

Katherine Kelly Vidal
*Director of the United States Patent and Trademark Office*

SEQUENCE LISTING

<160> NUMBER OF SEQ ID NOS: 10

<210> SEQ ID NO 1
<211> LENGTH: 9
<212> TYPE: PRT
<213> ORGANISM: Artificial sequence
<220> FEATURE:
<223> OTHER INFORMATION: nelipepimut-S peptide

<400> SEQUENCE: 1

Lys Ile Phe Gly Ser Leu Ala Phe Leu
1               5

<210> SEQ ID NO 2
<211> LENGTH: 9
<212> TYPE: PRT
<213> ORGANISM: Artificial sequence
<220> FEATURE:
<223> OTHER INFORMATION: variant of the nelipepimut-S peptide
<220> FEATURE:
<221> NAME/KEY: MOD_RES
<222> LOCATION: (4)..(4)
<223> OTHER INFORMATION: Abu

<400> SEQUENCE: 2

Lys Ile Phe Ala Ser Leu Ala Phe Leu
1               5

<210> SEQ ID NO 3
<211> LENGTH: 9
<212> TYPE: PRT
<213> ORGANISM: Artificial sequence
<220> FEATURE:
<223> OTHER INFORMATION: variant of the nelipepimut-S peptide
<220> FEATURE:
<221> NAME/KEY: MOD_RES
<222> LOCATION: (4)..(4)
<223> OTHER INFORMATION: Nva

<400> SEQUENCE: 3

Lys Ile Phe Val Ser Leu Ala Phe Leu
1               5

<210> SEQ ID NO 4
<211> LENGTH: 9
<212> TYPE: PRT
<213> ORGANISM: Artificial sequence
<220> FEATURE:
<223> OTHER INFORMATION: variant of the nelipepimut-S peptide
<220> FEATURE:
<221> NAME/KEY: MOD_RES
<222> LOCATION: (4)..(4)
<223> OTHER INFORMATION: Nle

<400> SEQUENCE: 4

Lys Ile Phe Leu Ser Leu Ala Phe Leu
1               5

<210> SEQ ID NO 5
<211> LENGTH: 9
<212> TYPE: PRT
<213> ORGANISM: Artificial sequence
<220> FEATURE:
<223> OTHER INFORMATION: variant of the nelipepimut-S peptide
<220> FEATURE:
<221> NAME/KEY: MOD_RES
<222> LOCATION: (7)..(7)
<223> OTHER INFORMATION: Abu

```
<400> SEQUENCE: 5

Lys Ile Phe Gly Ser Leu Ala Phe Leu
1               5

<210> SEQ ID NO 6
<211> LENGTH: 9
<212> TYPE: PRT
<213> ORGANISM: Artificial sequence
<220> FEATURE:
<223> OTHER INFORMATION: variant of the nelipepimut-S peptide
<220> FEATURE:
<221> NAME/KEY: MOD_RES
<222> LOCATION: (7)..(7)
<223> OTHER INFORMATION: Nva

<400> SEQUENCE: 6

Lys Ile Phe Gly Ser Leu Val Phe Leu
1               5

<210> SEQ ID NO 7
<211> LENGTH: 9
<212> TYPE: PRT
<213> ORGANISM: Artificial sequence
<220> FEATURE:
<223> OTHER INFORMATION: variant of the nelipepimut-S peptide
<220> FEATURE:
<221> NAME/KEY: MOD_RES
<222> LOCATION: (7)..(7)
<223> OTHER INFORMATION: Nle

<400> SEQUENCE: 7

Lys Ile Phe Gly Ser Leu Leu Phe Leu
1               5

<210> SEQ ID NO 8
<211> LENGTH: 9
<212> TYPE: PRT
<213> ORGANISM: Artificial sequence
<220> FEATURE:
<223> OTHER INFORMATION: variant of the nelipepimut-S peptide
<220> FEATURE:
<221> NAME/KEY: MOD_RES
<222> LOCATION: (8)..(8)
<223> OTHER INFORMATION: isophenylalanine

<400> SEQUENCE: 8

Lys Ile Phe Gly Ser Leu Ala Xaa Leu
1               5

<210> SEQ ID NO 9
<211> LENGTH: 214
<212> TYPE: PRT
<213> ORGANISM: Artificial sequence
<220> FEATURE:
<223> OTHER INFORMATION: Anti-HER2 Light chain (1 and 2)

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 10
<211> LENGTH: 450
<212> TYPE: PRT
<213> ORGANISM: Artificial sequence
<220> FEATURE:
<223> OTHER INFORMATION: Anti-HER2 Heavy chain (1 and 2)

<400> SEQUENCE: 10

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
                 20                  25                  30

Tyr Ile His Trp Val Arg Gln Ala Pro Gly Lys Gly Leu Glu Trp Val
             35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205
```

-continued

```
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
    435                 440                 445
Gly Lys
450
```